United States Patent
Badejo

(10) Patent No.: US 12,274,683 B2
(45) Date of Patent: Apr. 15, 2025

(54) TOPICAL GEL COMPOSITIONS OF NAPROXEN

(71) Applicant: Bayer HealthCare LLC, Indianola, PA (US)

(72) Inventor: Olufoyekemi Badejo, Bridgewater, NJ (US)

(73) Assignee: Bayer HealthCare LLC, Indianola, PA (US)

( * ) Notice: Subject to any disclaimer, the term of this patent is extended or adjusted under 35 U.S.C. 154(b) by 850 days.

(21) Appl. No.: 17/425,746

(22) PCT Filed: Jan. 8, 2020

(86) PCT No.: PCT/US2020/012654
§ 371 (c)(1),
(2) Date: Jul. 26, 2021

(87) PCT Pub. No.: WO2020/159676
PCT Pub. Date: Aug. 6, 2020

(65) Prior Publication Data
US 2022/0160667 A1    May 26, 2022

Related U.S. Application Data

(60) Provisional application No. 62/798,352, filed on Jan. 29, 2019.

(51) Int. Cl.
*A61K 31/192* (2006.01)
*A61K 9/00* (2006.01)
(Continued)

(52) U.S. Cl.
CPC .......... *A61K 31/192* (2013.01); *A61K 9/0014* (2013.01); *A61K 9/06* (2013.01); *A61K 47/02* (2013.01); *A61K 47/10* (2013.01); *A61K 47/183* (2013.01); *A61K 47/32* (2013.01); *A61K 47/38* (2013.01); *A61P 29/00* (2018.01)

(58) Field of Classification Search
CPC ...... A61K 31/192; A61K 9/0014; A61K 9/06; A61K 47/02; A61K 47/10; A61K 47/183; A61K 47/32; A61K 47/38; A61K 47/18; A61K 47/34; A61P 29/00
See application file for complete search history.

(56) References Cited

U.S. PATENT DOCUMENTS

2010/0099766 A1    4/2010   Zhang et al.

FOREIGN PATENT DOCUMENTS

| EP | 872247 A1 * | 10/1998 | ........... A61K 31/192 |
| EP | 2289493 A1 | 3/2011 | |

(Continued)

OTHER PUBLICATIONS

International Search Report and Written Opinion, mailed on Apr. 7, 2020, for Application No. PCT/US2020/012654, filed on Jan. 8, 2020, 15 pages.

*Primary Examiner* — Deborah D Carr

(57) ABSTRACT

The present disclosure relates generally to topical analgesic compositions comprising nonsteroidal anti-inflammatory drugs, and more specifically to topical gel compositions of naproxen in combination with select neutralizing agents, thereby having enhanced skin permeation and skin retention properties as well as improved aesthetics upon application and drying.

29 Claims, 9 Drawing Sheets

(51) Int. Cl.
*A61K 9/06* (2006.01)
*A61K 47/02* (2006.01)
*A61K 47/10* (2017.01)
*A61K 47/18* (2017.01)
*A61K 47/32* (2006.01)
*A61K 47/38* (2006.01)
*A61P 29/00* (2006.01)

(56) References Cited

FOREIGN PATENT DOCUMENTS

GB 1291386 A 10/1972
WO 0072827 A2 12/2000

\* cited by examiner

TOPICAL GEL COMPOSITIONS OF NAPROXEN

FIELD OF THE INVENTION

The present disclosure relates generally to topical analgesic compositions comprising non-steroidal anti-inflammatory drugs, and more specifically to topical gel compositions of naproxen having enhanced skin permeation and skin retention properties, as well as improved aesthetics upon application and drying.

BACKGROUND

Non-steroidal anti-inflammatory drugs (NSAIDs), despite being a commonly and widely used class of analgesics, have limited availability in topical pain-relieving formulations. Topical analgesic compositions may be preferable to the corresponding oral dosage forms of the same active pharmaceutical ingredient, for example, in instances in which the pain is localized, or in which systemic distribution is not recommended for the patient due to adverse effects associated with the active ingredient and other contraindications.

However, the many potential advantages of topical analgesic compositions over oral formulations are often offset by the poor skin permeation and retention characteristics of the active compounds themselves due to the skin barrier properties. As a result, the efficacy of such topical compositions is often inconsistent and low, leading to a lesser pain-relieving effect per use and necessitating repeated applications to the same target site to achieve the desired analgesic effect. In addition, a variety of sensory and aesthetic factors that are important for topical applications, such as spreadability during application and transparency on the skin after drying, are highly dependent upon the selection of excipients in the topical analgesic compositions. Consideration of these additional factors makes the preparation of topical analgesics having the desired skin permeation and retention properties significantly more difficult.

Few topical analgesic compositions that manage to achieve an appropriate balance of permeation and retention for localized drug delivery to skin tissue while also preserving sensory and aesthetic appeal currently exist. Thus, there is a need for topical analgesic compositions of non-steroidal anti-inflammatory analgesics, such as naproxen, that achieve greater skin permeation and retention, thereby providing increased therapeutic effect per application without forgoing the sensory and aesthetic characteristics of the formulations.

BRIEF SUMMARY

In one aspect, provided herein is a topical gel composition comprising: naproxen ammonium, one or more gelling agents; and water. In some embodiments, the topical gel composition has a total concentration of naproxen between 1% w/w and 10% w/w. In some embodiments, the topical gel composition comprises propylene glycol and polyethylene glycol. In certain embodiments, the topical gel composition is a clear gel.

In another aspect, provided herein is a method of treating muscle pain or joint pain in a patient in need thereof, comprising applying a topical gel composition as described herein, to the patient's skin at the site of pain. In some embodiments of the method, the muscle pain or joint pain is associated with arthritis, sprains, strains, bruises, or backache.

In still yet another aspect, provided herein is a method of preparing the topical gel compositions as described herein, comprising: combining a gelling agent and water to provide a gel mixture; adding ammonia solution to the gel mixture; combining naproxen free acid, one or more alcoholic solvents, optionally a film-forming agent, and optionally an antioxidant to provide an alcohol mixture; and combining the alcohol mixture with the gel mixture to provide the topical gel composition.

DESCRIPTION OF THE FIGURES

FIG. 6A shows Von Frey thresholds from Von Frey nociception analysis as a function of time for various topical formulations, including the control formulations. FIG. 6B shows the observed mean absolute Von Frey thresholds, expressed as areas the under curves, for the entire duration of the Von Frey analysis. FIG.

6C shows the corresponding ankle caliper measurements of differences between the right and left hindpaws of the rat subjects over the course of the inflammation study. FIG. 6D shows the mean ankle caliper differences, expressed as areas under the curves, for the various formulations.

FIG. 7A shows Von Frey thresholds from Von Frey nociception analysis as a function of time for various topical formulations, including control formulations. FIG. 7B shows the observed mean absolute Von Frey thresholds, expressed as areas the under curves, for the entire duration of the Von Frey analysis. FIG. 7C shows the corresponding ankle caliper measurements of differences between the right and left hindpaws of the rat subjects over the course of the inflammation study. FIG. 7D shows the mean ankle caliper differences, expressed as areas under the curves, for the various formulations.

FIGS. 8A and 8B show the mean level of naproxen (in ng/g) concentrated in the top 8 mm of muscle tissue and the remaining muscle tissue, respectively. FIGS. 8C and 8D show the mean level of naproxen (in ng/g) in skin tissue overall and in the subcutaneous tissues, respectively.

DETAILED DESCRIPTION

Figure 1A:
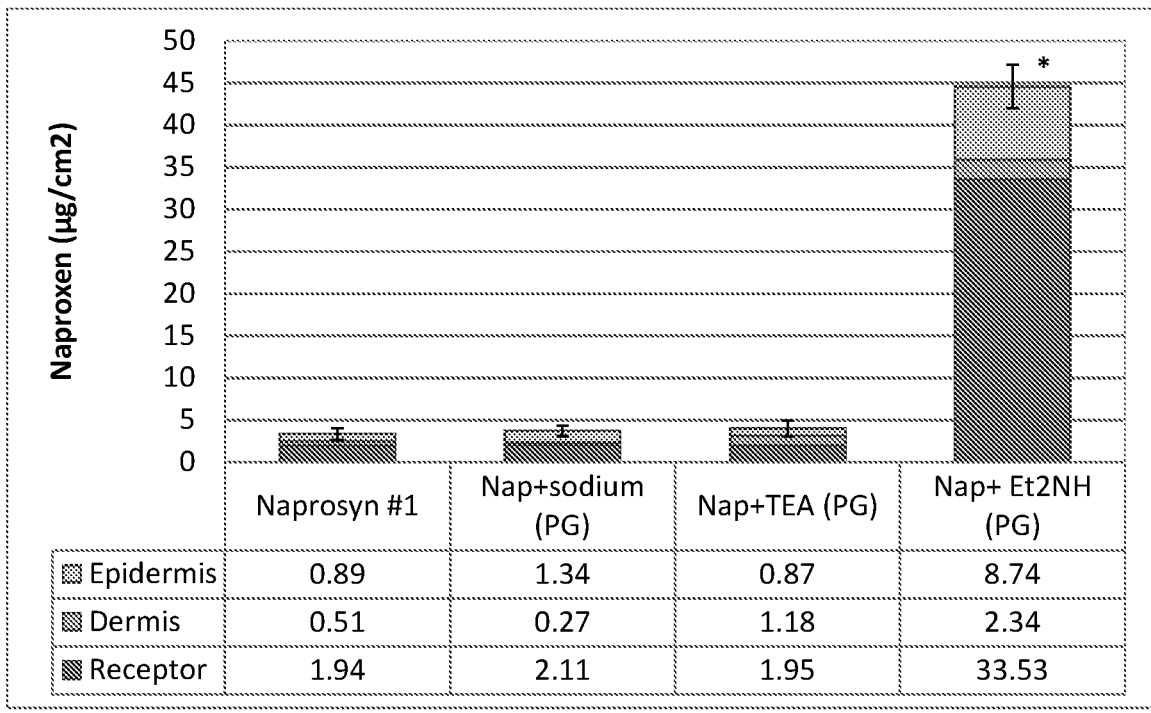
FIGS. 1A and 1B depict skin distribution profiles (epidermis and dermis) and receptor chamber permeation of naproxen (in $\mu g/cm^2$) of different topical gel formulations containing naproxen in combination with various neutralizing agents with propylene glycol (PG) as a solvent as observed in in vitro skin permeation tests (IVPT) using a Franz diffusion cell. Naprosyn® topical gel was also evaluated. Statistically significant differences between the different formulations have been denoted by an asterisk in the respective figures.

Non-steroidal anti-inflammatory drugs (NSAIDs) are regularly used to relieve pain associated with a broad array of inflammatory conditions, although their use has been associated with the co-occurrence of certain adverse effects and other risk factors. Yet, despite the side effects and risk factors associated with this class of drugs, NSAIDs remain some of the most frequently administered analgesics worldwide, especially in oral dosage forms.

Topical administration of NSAIDs is one avenue to reduce undesirable side effects associated with the corresponding oral dosage forms. Additionally, topical NSAID compositions may also provide the benefit of fast-acting, localized pain relief directly at the site of injury or pain, in contrast to the delayed analgesic effect expected with oral administration and systemic distribution. There currently exist few options for topical analgesic compositions containing NSAIDs, and even fewer of which provide consistent, predictable pain relief in formulations that also possess acceptable sensory and aesthetic attributes for external application.

One of the many impediments to preparing highly efficacious topical NSAID formulations is the ability of the active ingredients to pass through the outer layer of skin to which they are applied in order to reach the underlying site of inflammation. The development of effective topical NSAID formulations requires the penetration of the analgesic into and through the outer layer of the skin, i.e., the stratum corneum barrier, and accumulation in the inner layers of the epidermis and dermis, for maximum pain relief. Consequently, successful drug delivery into the skin depends to a significant degree upon the physicochemical properties of the drug molecule itself, including molecular weight, ionizability and lipophilicity.

Although intrinsic physicochemical properties largely influence an active ingredient's capacity to permeate into and accumulate in the skin, the penetration of the active ingredient into the underlying skin tissue may also be modulated by the specific composition of the topical drug formulation. Previous efforts to improve topical drug delivery have focused on increasing skin permeation through the addition of excipients that enhance the movement of the active ingredient through the epidermis and dermis. For example, skin penetration enhancers are one category of excipients utilized in many transdermal formulations to reduce skin barrier resistance. However, many skin penetration enhancers, such as dimethylsulfoxide, increase diffusion of active pharmaceutical ingredients with little to no regard for accumulation or retention of the analgesic compounds in the skin and underlying muscle tissue. As a result, penetration enhancers are more useful in transporting the analgesic through the skin and into the bloodstream rather than delivering the active ingredient to the deeper skin tissues for localized administration.

Further complicating the development of topical analgesic compositions are the sensory and aesthetic aspects of these formulations. As topical compositions are applied externally, both the visual and tactile properties of such compositions will strongly influence their consumer appeal and patient compliance in utilizing the topical medications. Any number of properties of the topical analgesic formulation may be relevant to consumer appeal and patient compliance such as ease of application, a smooth and non-greasy feel on the skin, acceptable or no fragrance, speed of drying on the skin after application, and invisibility after drying. For example, a topical formulation which does not dry quickly or dry clear on the skin following application may be sufficiently unappealing to deter its future use.

Another major source of difficulty in preparing an acceptable topical analgesic composition is that the skin permeation and retention properties as well as the sensory and aesthetic aspects are highly influenced by the excipients employed in the topical formulation. Excipients that improve the composition from a therapeutic standpoint may do so at the expense of aesthetic and sensory attributes, or even other important pharmacokinetic properties. For example, one excipient added to a topical formulation may increase skin permeation but negatively impact skin accumulation, while another excipient may enhance skin retention but reduce the transparency of the formulation. Due to the difficulty of achieving desirable levels of skin permeation and skin retention in topical compositions, it is not uncommon for therapeutic efficacy to be prioritized over consumer appeal and patient compliance. As a result, sensory and aesthetic properties are very frequently relegated to an afterthought in formulation development.

Presently, there is a need for topically applied alternatives to traditional oral dosage forms of NSAIDs, and more specifically topical compositions of naproxen that possess superior skin permeation and retention characteristics as compared to existing topical analgesics formulations. There is a further need for topical naproxen compositions that not only achieve these improved skin drug delivery properties but that do so without negatively impacting aesthetic and sensory qualities of the compositions for patient compliance.

Described herein are topical gel compositions of naproxen having increased skin permeation and skin retention properties for greater therapeutic efficacy. The present topical gel compositions achieve enhanced permeation and accumulation of naproxen in the skin by combining naproxen with specific neutralizing agents to produce the corresponding salt forms of naproxen in situ. The use of these specific naproxen salt forms, such as naproxen ammonium, has been surprisingly observed to increase the propensity of naproxen to diffuse into and remain in the lower skin tissues for augmented analgesic effect.

Though advantageous for increasing skin permeation and skin retention, the inclusion of certain neutralizing agents, such as ammonium hydroxide, has been found to be less beneficial to the composition from an aesthetic standpoint. Substantial precipitation of a white residue on the skin, possibly attributable to the naproxen free acid or film-forming agent, was also observed after application and drying of the naproxen formulations containing ammonium hydroxide. However, the further addition of combinations of particular solvents, such propylene glycol and polyethylene glycol, to the topical formulations has been found minimize the appearance of the unwanted white residue on the skin. Thus, the present disclosure also provides topical gel compositions comprising specific naproxen salts and solvents that exhibit enhanced skin aesthetics, including drying and remaining clear on the skin after application, as well as improved skin permeation and retention properties.

The following description sets forth exemplary methods, parameters and the like. It should be recognized, however, that such description is not intended as a limitation on the scope of the present disclosure but is instead provided as a description of exemplary embodiments.

Topical Gel Compositions

In one aspect, provided herein are topical compositions comprising particular naproxen salts and having enhanced skin permeation and retention properties. More specifically, provided herein are topical gel compositions prepared by combining naproxen with one or more neutralizing agents to form particular naproxen salts in situ which achieve increased skin permeation and skin retention for enhanced therapeutic effect. The present disclosure also provides for topical gel compositions comprising particular naproxen salts and certain combinations of excipients to produce the desired skin permeation and retention properties, as well as the desired transparency of the gel following application and drying on the skin.

Naproxen is an active compound in the class of non-steroidal anti-inflammatory drugs (NSAIDs), which are widely used to treat inflammation-related disorders. Naproxen possesses further antipyretic and analgesic properties in addition to its anti-inflammatory effects, and is used to treat various ailments including but not limited to minor pain of arthritis, menstrual cramps, muscular aches, backache, headache, toothache, and the common cold. However, use of naproxen can result in many of the adverse effects associated with non-selective NSAIDs and may be further contraindicated with various medications and conditions. Combination treatments of naproxen with other actives to combat these adverse effects, unfortunately, do not entirely eliminate them nor do they address other contraindications. In some embodiments, the topical gel composition comprises naproxen.

It should be acknowledged, however, that the compositions of the present disclosure may also be suitable for the topical application of other drugs similar to naproxen in pain relieving effect, mechanism of action, chemical structure, physicochemical properties, or any combinations thereof, in lieu of naproxen as the primary active ingredient. Alternatively, it should be recognized that the topical gel compositions of the present disclosure may be suitable for topical application of pharmaceutical combinations comprising multiple active pharmaceutical ingredients, in which naproxen may be one such ingredient.

Naproxen Salts and Neutralizing Agents

A widespread issue in preparing effective topical analgesic compositions is ensuring a consistent dosage of the analgesic with respect to the quantity of active in the formulation and each application. The actual amount of the active ingredient (by weight percentage) absorbed into and retained by the skin is often only a small fraction of the amount of the active ingredient present in the topical formulation and applied to the skin. In its most common oral dosage forms, naproxen is typically utilized in its free acid or sodium salt forms. However, due to the lipophilic nature of the skin, topical formulations containing the naproxen free acid and naproxen sodium have been observed to exhibit undesirably low skin permeation and/or retention characteristics.

It has been surprisingly observed that the use of particular non-sodium naproxen salts, such as naproxen ammonium, in topical analgesic compositions achieves a balance of skin permeation and skin retention properties suitable for successful drug delivery into deeper skin tissues. Moreover, the topical gel compositions of the present disclosure containing these naproxen salts exhibit remarkable increases in both skin permeation and skin retention of naproxen as compared to the naproxen sodium salt. Consequently, the topical gel compositions comprising the naproxen salts described herein have improved skin permeation and retention characteristics, thereby producing a dosage of naproxen that is more consistent per application that is more directly proportional to the amount of naproxen present in the formulation.

The topical gel compositions of the present disclosure may contain one or more naproxen salts. In some embodiments wherein the topical gel composition comprises one or more naproxen salts, the one or more naproxen salts include at least naproxen ammonium. In some embodiments, the topical gel composition comprises naproxen ammonium, naproxen triethanolamine, naproxen diethylammonium, naproxen potassium, or naproxen sodium, or any combinations thereof. In certain embodiments, the topical gel composition comprises naproxen ammonium, naproxen triethanolamine, naproxen diethylammonium, or naproxen potassium, or any combinations thereof. In still yet other embodiments, the topical gel composition does not contain naproxen sodium.

The naproxen salts described herein, which possess improved physicochemical characteristics for enhanced skin diffusion and accumulation, are produced in situ in the topical gel composition through the combination of one or more neutralizing agents with the naproxen free acid. For example, the inclusion of ammonia solution as a neutralizing agent in topical naproxen compositions has been unexpectedly found to increase the skin permeation through the epidermis and retention in both the epidermis and dermis by virtue of the naproxen ammonium salt formed. In some embodiments, the one or more neutralizing agents comprises an ammonia solution ($NH_3$ (aq), or $NH_4OH$, ammonium hydroxide solution), triethanolamine, diethylamine, or potassium hydroxide (KOH), or any combinations thereof.

As the particular naproxen salts of the present disclosure are formed in situ by combining the naproxen free acid and one or more neutralizing agents, the one or more neutralizing agents and the corresponding naproxen salts may co-exist in the topical gel compositions of the present disclosure. For example, in some embodiments wherein the topical gel composition comprises naproxen ammonium, the topical gel composition comprises ammonia solution. In other embodiments wherein the topical gel composition comprises naproxen triethanolammonium, the topical gel composition comprises triethanolamine. In still other embodiments wherein the topical gel composition comprises naproxen diethylammonium, the topical gel composition comprises diethylamine. In certain embodiments wherein the topical gel composition comprises naproxen potassium, the topical gel composition comprises potassium hydroxide. It should be recognized that in topical gel compositions also comprising naproxen sodium salt, the naproxen sodium salt may be added directly to the composition or prepared in situ by combining naproxen as the free acid with, for example, sodium hydroxide.

It should also be recognized that naproxen may exist in both its free acid form and one or more salt forms in the topical gel compositions described herein depending upon the identity and quantity of neutralizing agent(s) used. In certain embodiments, the topical gel composition comprises naproxen in the free acid form, naproxen in one or more salt forms, or any combinations thereof.

In view of the co-existence of the naproxen free acid and naproxen salts in the topical gel compositions described herein, it is useful to describe the topical gel composition by the total concentration of naproxen present in the topical gel composition. The total concentration of naproxen in the topical gel compositions described herein is the sum of the individual concentration of the naproxen free acid, if present, and the individual concentrations of any salts thereof. In some embodiments, the topical gel composition has a total concentration of naproxen of at least about 1% w/w or at least about 5% w/w. In other embodiments, the topical gel composition has a total concentration of naproxen less than or equal to about 20% w/w or less than or equal to about 10% w/w. In certain embodiments, the topical gel composition has a total concentration of naproxen of about 1% w/w, about 5% w/w, about 10% w/w, or about 20% w/w. In certain embodiments, the topical gel composition has a total concentration of naproxen of about 10% w/w. In still other embodiments, the topical gel composition has a total concentration of naproxen between about 1% w/w and about 20% w/w, between about 1% w/w and about 10% w/w, between about 5% w/w and about 20% w/w, or between about 5% w/w and about 10% w/w.

It may also be useful to consider the individual concentrations of the free acid and salt forms of naproxen in the topical gel composition. The individual concentrations of the free acid and corresponding salt form(s) of naproxen present in the topical gel composition may depend upon a number of factors including but not limited to the basicity of the neutralizing agent(s) and/or the quantity of neutralizing agent(s) used to prepare the topical gel composition. The in situ formation of naproxen salts in the topical gel compositions described herein may or may not be stoichiometric with respect to the molar amounts of naproxen free acid and neutralizing agent(s) used to prepare the composition.

In some embodiments, the topical gel composition has a concentration of naproxen ammonium of at least about 1% w/w or at least about 5% w/w. In other embodiments the topical gel composition has a concentration of naproxen ammonium of less than or equal to about 10% w/w or less than or equal to about 20% w/w. In some embodiments, the topical gel composition has a concentration of naproxen triethanolammonium of at least about 1% w/w or at least about 5% w/w. In other embodiments, the topical gel composition has a concentration of naproxen triethanolammonium of less than or equal to about 10% w/w or less than or equal to about 20% w/w. In some embodiments, the topical gel composition has a concentration of naproxen diethylammonium of at least about 1% w/w or at least about 5% w/w. In other embodiments the topical gel composition has a concentration of naproxen diethylammonium of less than or equal to about 10% w/w or less than or equal to about 20% w/w. In some embodiments, the topical gel composition has a concentration of naproxen potassium of at least about 1% w/w or at least about 5% w/w. In other embodiments the topical gel composition has a concentration of naproxen potassium of less than or equal to about 10% w/w or less than or equal to about 20% w/w.

Excipients

In some embodiments, the topical gel composition of the present disclosure further comprises pharmaceutically acceptable excipients. For topically administered compositions, the selection of excipients will strongly influence not only the skin permeation and retention properties of the topical composition, but also the sensory feel and appearance of the composition on the skin. As noted above, an unattractive appearance or unpleasant texture of topical compositions on the skin following application may be a major deterrent to patient compliance. The selection of excipients should be specially tailored to produce the desired sensory and aesthetic properties of the final topical gel composition.

Gel compositions are often easy to apply, have smooth skin feel, and have an aesthetically appealing translucent or transparent appearance. Consequently, topical gel compositions benefit from higher patient acceptance as compared to other topical forms including ointments, or emulsion-type creams or lotions. The topical compositions of naproxen in the present disclosure are formulated as gel compositions. As such, the topical compositions described herein contain excipients suitable for the preparation of gel compositions.

In some embodiments, the topical gel composition comprises one or more gelling agents. Gelling agents confer physical structure, texture, viscosity, adhesion and other properties commonly associated with gels to the compositions described herein. Gelling agents may include, but are not limited to, natural gums (e.g., gum Arabic, tragacanth), cellulose derivatives (e.g., methyl cellulose, hydroxyethyl cellulose, hydroxypropyl methylcellulose, carboxymethyl cellulose), alginates, pectins, carrageenates, agar, and gelatin. In some embodiments, the topical gel composition comprises at least about 1.0% w/w or at least about 2.0% w/w one or more gelling agents. In other embodiments, the topical gel composition comprises less than or equal to about 5.0% w/w or less than or equal to about 10.0% w/w one or more gelling agents.

Particular gelling agents, such as cellulosic agents, may be especially useful to achieve the desired sensory properties, such as viscosity, of the topical gel compositions described herein. For example, in some embodiments wherein the topical gel composition comprises one or more gelling agents, the one or more gelling agents comprise hydroxyethylcellulose (HEC), hydroxypropyl methylcellulose (HPMC), or carboxymethyl cellulose (CMC), or any combination thereof. In certain embodiments, the topical gel composition comprises hydroxyethylcellulose. In certain embodiments wherein the topical gel composition comprises hydroxyethylcellulose, the topical gel composition comprises between about 1.0% w/w and about 2.0% w/w hydroxyethylcellulose. In yet other embodiments, the topical gel composition comprises about 1.4% w/w hydroxyethylcellulose. Additionally, particular grades of certain gelling agents having certain solubility, hydration time, percentage of cross-linking, etc., may be selected to provide topical gel composition having acceptable sensory characteristics.

In some embodiments, the topical gel composition comprises one or more film-forming agents. As with gelling agents, film-forming agents are often included in pharmaceutical and cosmetic formulations to achieve, among other things, the desired compositional consistency and smooth coating properties. Common film-forming agents may include but are not limited to polyvinylpyrrolidone (PVP, or povidone), acrylates, acrylamides, and copolymers. In certain embodiments, the one or more film-forming agents comprise vinyl pyrrolidone-vinyl acetate copolymer, or copovidone, or a combination thereof. In some embodiments, the topical gel composition comprises copovidone.

For topical applications, film-forming agents contribute to the overall smoothness, or silky feel, of a topical composition. In some embodiments, the topical gel composition comprises between about 0% w/w and about 1.0% w/w one or more film-forming agents. In certain embodiments, the topical gel composition comprises less than about 1.0% w/w copovidone. In other embodiments, the topical gel composition does not contain film-forming agents. In certain embodiments, the topical gel composition contains 0% w/w film-forming agent(s).

In addition to gelling agents and film-forming agents, the topical gel compositions herein also contain one or more liquid excipients that serve as a medium for the gelling agents, thereby providing the semi-solid, viscous properties of a gel. In some embodiments, the topical gel composition comprises water. In other embodiments, the topical gel composition is an aqueous gel composition. In certain embodiments, the topical gel composition comprises at least about 25% w/w, at least about 30% w/w, or at least about 35% w/w water. In some embodiments, the topical gel composition comprises less than or equal to about 40% w/w or less than or equal to about 50% w/w water.

Pharmaceutically acceptable alcoholic solvents may also be incorporated into the topical gel composition. Alcoholic solvents can serve a number of functionalities in a topical gel composition, including facilitating the dispersion of the water-insoluble components in the gel, promoting water retention, modulating viscosity, and preserving the compositions against microbial growth. In some embodiments, the topical gel compositions described herein comprise one or more alcoholic solvents. In certain embodiments, the one or more alcoholic solvents are selected from the group consisting of ethanol, propylene glycol, polyethylene glycol, and any combinations thereof. In certain embodiments, the topical gel composition of the present disclosure is an aqueous alcoholic gel composition. In other embodiments, the topical gel composition is a hydroalcoholic gel composition.

The use of alcoholic solvents having lower vapor pressures than water, such as ethanol, may also contribute to the fast-drying properties of the gel, which is highly desirable for patient compliance. In some embodiments, the topical gel composition comprises ethanol. In some embodiments, the topical gel composition comprises at least about 20% w/w ethanol. In other embodiments, the topical gel composition comprises at least about 30% w/w ethanol. In certain embodiments, the topical gel composition comprises about 30% w/w ethanol. In still other embodiments, the topical gel composition comprises less than or equal to 50% w/w ethanol.

In addition to the above functionalities, other alcoholic solvents, such as propylene glycol and polyethylene glycol, may be further useful to maintain formulation stability—e.g., uniform dispersion and prevention of phase separation or crystallization of the active ingredient—and to modify the present compositions to produce the desired sensory characteristics—e.g., smoothness on the skin during and after application, reduced greasiness and minimal stickiness.

In some embodiments, the topical gel composition comprises propylene glycol. In some embodiments, the topical gel composition comprises less than or equal to about 10% w/w propylene glycol. In other embodiments, the topical gel composition comprises less than or equal to about 5% w/w propylene glycol. In certain embodiments, the topical gel composition comprises between about 1% w/w and 5% w/w propylene glycol. In still other embodiments, the topical gel composition comprises about 2.5% w/w propylene glycol.

In still other embodiments, the topical gel composition comprises polyethylene glycol, also known as PEG or Macrogol. Particular grades of polyethylene glycol may be especially useful in the topical gel compositions described herein. Grades of polyethylene glycol may be identified, for example, by weight average molecular weight. In some embodiments, the topical gel composition comprises polyethylene glycol, wherein the polyethylene glycol has a weight average molecular weight of between about 200 g/mol and about 800 g/mol. In certain embodiments, the polyethylene glycol has a weight average molecular weight of between about 400 g/mol and about 600 g/mol.

In some embodiments, the topical gel composition comprises at least about 10% w/w polyethylene glycol. In certain embodiments, the topical gel composition comprises at least about 2.5% w/w polyethylene glycol, wherein the polyethylene glycol has a weight average molecular weight of about 400 g/mol. In other embodiments, the topical gel composition comprises less than or equal to about 20% w/w polyethylene glycol. In certain embodiments, the topical gel composition comprises between about 2.5% w/w and about 20% w/w polyethylene glycol. In certain embodiments, the topical gel composition comprises about 10% w/w polyethylene glycol.

As described herein, the combination of naproxen with one or more neutralizing agents to produce particular salts in situ has been observed to provide unexpected improvements to the skin permeation and retention of naproxen in topical gel compositions. However, the enhancement in skin diffusion and accumulation was also accompanied by precipitation of a highly visible, white residue on the skin after drying for the very same neutralizing agents.

It has been found that the use of propylene glycol and polyethylene glycol together have observed to modify the aesthetic properties of the topical gel compositions sufficiently to counteract the formation of the white precipitate after drying, without significantly impacting the balance of skin permeation and retention characteristics, and other sensory and aesthetic attributes. In other embodiments, the topical gel composition comprises propylene glycol and polyethylene glycol. In certain embodiments, the topical gel composition comprises at least about 10% w/w propylene glycol and at least about 10% w/w polyethylene glycol. In other embodiments, the topical gel composition comprises at least 20% w/w of a combination of propylene glycol and polyethylene glycol. In yet other embodiments, the topical gel composition comprises between about 1% w/w and about 5% w/w propylene glycol and between about 2.5% w/w and about 20% w/w polyethylene glycol. In still yet other embodiments, the topical gel composition comprises between about 5% w/w and about 20% w/w, or between about 10% w/w and about 20% w/w of a combination propylene glycol and polyethylene glycol. In certain embodiments, the topical gel composition comprises about 2.5% w/w propylene glycol and about 10% w/w polyethylene glycol.

Additional Ingredients

In some embodiments, the topical gel composition may comprise further ingredients, including but not limited to preservatives and antioxidants. The use of preservatives and antioxidants may help to maintain the integrity of the active pharmaceutical ingredients, inhibit microbial growth, and prevent decomposition of the actives and excipients via oxidative reactions during storage. In some embodiments, the topical gel composition comprises one or more pharmaceutically acceptable excipients selected from the group consisting of an antioxidant, a preservative, and fragrance.

For example, in some embodiments, the topical gel composition comprises one or more antioxidants. In some embodiments wherein the topical gel composition comprises one or more antioxidants, the topical gel composition comprises sodium metabisulfite ($NaS_2O_5$), ethylenediaminetetraacetic acid (EDTA), or sodium propionate, or any mixtures thereof. In some embodiments the topical gel composition comprises sodium metabisulfite. In other embodiments, the topical gel composition comprises sodium propionate. In still other embodiments, the topical gel composition comprises ethylenediaminetetraacetic acid. In certain embodiments, the topical gel composition comprises sodium metabisulfite and ethylenediaminetetraacetic acid.

In certain embodiments, the topical gel composition comprises at least about 0.1% w/w or at least about 0.25% w/w antioxidant. In other embodiments, the topical gel composition comprises less than or equal to about 0.75% w/w antioxidant. In certain embodiments, the topical gel composition comprises between about 0.1% w/w and about 0.75% w/w, between about 0.25% w/w and about 0.75% w/w, between about 0.5% w/w and about 0.75% w/w or between about 0.25% w/w and about 0.5% w/w antioxidant. In some embodiments, the topical gel composition comprises between about 0.1% w/w and about 0.25% w/w sodium metabisulfite. In certain embodiments, the topical gel composition comprises about 0.25% w/w sodium metabisulfite. In other embodiments, the topical gel composition comprises between about 0.1% w/w and about 0.25% w/w EDTA. In certain embodiments, the topical gel composition comprises about 0.17% w/w EDTA. In still yet other embodiments, the topical gel composition comprises about 0.25% w/w sodium metabisulfite and about 0.17% w/w EDTA.

In some embodiments, the topical gel composition comprises a preservative. In certain embodiments, the topical gel comprises ethylenediaminetetraacetate (EDTA). In some embodiments, the topical gel composition comprises between about 0.05% w/w and about 0.30% w/w EDTA. In certain embodiments, the topical gel composition comprises between about 0.10% w/w and about 0.20% w/w EDTA.

The topical gel composition may include further ingredients, such as dyes, fragrance, or sensates which make the composition more appealing to consumers and patients. In some embodiments, the topical gel composition may comprise fragrance.

In other embodiments, the topical gel composition may comprise one or more sensates. Sensates may be additional ingredients that impart a sensorial cue, such as cooling, warming or tingling, or even numbing, to the patient's skin in topical formulations. In some embodiments, the topical gel composition comprises one or more sensates, wherein the one or more sensates are selected from the group consisting of cooling sensates, warming sensates, tingling sensates, and numbing sensates. In certain embodiments wherein the topical gel composition comprises one or more sensates, the one or more sensates are selected from the group consisting of menthol and menthol derivatives (e.g., isomenthol, neomenthol, neoisomenthol, menthoglycol para-menthoxy-3,8-propanediol, isopulegol), capsaicin, other capsaicinoids (e.g., dihydrocapsaicin, nordihydrocapsaicin, homocapsaicin, and homodihydrocapsaicin) camphor, eucalyptol, cinnamaldehyde, vanilloid derivatives such as vanillyl alcohol alkyl ethers (e.g., vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol n-hexyl ether, vanillyl amyl ether, vanillyl alcohol methyl ether, vanillyl alcohol ethyl ether, vanillyl isoamyl ether), gingerol, zingerone, shogaol, piperine, and any combinations thereof. In some embodiments, the one or more sensates are colorless and/or odorless.

In addition, the topical gel composition may contain further agents, including humectants. For example, in some embodiments, the topical gel composition comprises glycerin. In certain embodiments, the topical gel composition comprises between about 0.1% w/w and about 1.0% w/w glycerin. In certain embodiments, the topical gel composition comprises about 0.50% w/w glycerin.

Physical Properties of the Topical Gel Compositions

The topical gel compositions of the present disclosure may also be characterized by additional properties including, but not limited to, pH, viscosity, spreadability, skin adhesion, and homogeneity.

The acidity and/or basicity of a topical gel composition may have a significant effect on the chemical integrity of the active pharmaceutical ingredient, the physical stability of the gel composition, and the skin permeation and retention properties of the gel composition, among other attributes. In some embodiments, the present disclosure provides topical gel compositions having a pH between about pH 6 and about pH 9, or between about pH 7 and about pH 9. The pH of the topical gel composition may be the intrinsic additive pH of the active pharmaceutical ingredient, one or more neutralizing agents, and pharmaceutically acceptable excipients, or may be the resultant pH achieved with the addition of a buffering agent.

The viscosity of the topical gel compositions described herein may also be considered, as viscosity and, more generally, the consistency are important not only for manufacturing but also patient compliance. In some embodiments, the topical gel composition has a viscosity of at least about 6,000 centipoise (cP), at least about 7,000 cP, or at least about 8,000 cP. In other embodiments, the topical gel composition has a viscosity of less than or equal to about 11,000 cP. In certain embodiments, the topical gel composition has a viscosity of between about 6,000 cP and about 11,000 cP, between about 7,000 cP and about 11,000 cP, or between about 8,000 cP and about 11,000 cP.

Skin Permeation and Retention Properties

The topical gel compositions described herein have enhanced skin permeation and retention properties, and consequently improved therapeutic efficacy per application for pain relief. The observed improvements in skin permeation and skin retention are attributable to particular naproxen salts utilized in the topical gel compositions.

The skin permeation and skin retention properties of the topical gel compositions described herein may be determined by an in vitro permeation test (IVPT) using, for example, a Franz diffusion cell or equivalent diffusion cell or permeation test method as recognized in the art. The in vitro permeation tests performed in the present disclosure are conducted using Franz diffusion cells.

A Franz diffusion cell contains two main compartments, a donor chamber and a receptor chamber, separated by a permeable, porous membrane, with the receptor chamber accessible through a sampling port. The pharmaceutical formulation to be tested is loaded onto the donor chamber side of the porous membrane and the receptor chamber is filled with solvent, typically a neutral pH buffer solution, which is further stirred and maintained at a constant temperature throughout the test. The skin permeation and retention properties of a pharmaceutical formulation can be assessed in a Franz diffusion cell by measuring the diffusion of the active pharmaceutical ingredient in the formulation from the starting donor chamber, through the permeable membrane, and into the connected receptor chamber by sampling the receptor chamber solvent at various time points throughout the test. The final concentrations of the active pharmaceutical ingredient absorbed into the membrane, diffused into the receptor chamber and remaining in the donor chamber may also be determined upon completion of the test using High Pressure Liquid Chromatography (HPLC) or Liquid Chromatography with Tandem Mass Spectrometry (LC-MS-MS).

In vitro permeation tests may, in general, be conducted using a wide set of variables and parameters, including but not limited to the loading amount of topical gel composition in the donor chamber, thickness and surface area of the membrane, membrane type (human or synthetic), the solvent used in the receptor chamber, temperature and stir rate in the receptor chamber, and sampling schedule. The in vitro permeation tests conducted on the topical gel compositions described herein were performed with the parameters as defined in the table below.

| Franz Diffusion Cell In Vitro Permeation Test Parameters | |
|---|---|
| Parameter | Value |
| DONOR CHAMBER | |
| Loading Amount of Topical Gel Composition | 6.4 mg per 0.64 cm$^2$ |
| MEMBRANE | |
| Membrane type | Dermatomed human skin |
| Thickness | 300-500 µm |
| RECEPTOR CHAMBER | |
| Solvent | 1X, PBS buffer |
| Volume | 5 mL |
| pH | pH 7.4 |
| Temperature | 37° C. |
| Stir Rate | 600 rpm |
| SAMPLING SCHEDULE | |
| Time Point Increment | 3 h, 6 h, 12 h, 22 h, and 24 h |
| Total Duration of Test | 24 h |

The penetration, permeation and retention (accumulation) properties of the topical gel compositions described may be characterized by a number of metrics known in the art, including total amount of drug absorbed after 24 hours, dermal absorption (epidermis plus dermis), and flux.

For example, in some embodiments, the topical gel composition may be characterized by the observed partitioning of naproxen across different regions of the Franz diffusion cell (donor chamber, membrane, and receptor chamber) after a steady-state equilibrium has been achieved in the cell, which can be determined by a constant concentration of naproxen in the receptor chamber solvent, as measured over several time points. The partitioning of the active pharmaceutical ingredient in the different regions of the cell may be described as percentages of the total active pharmaceutical ingredient transferred into the membrane and receptor chamber per the total amount of the gel composition applied. In certain embodiments wherein the permeable membrane is excised human skin, the partitioning of the active pharmaceutical ingredient in the permeable membrane may be further described as a percentage of the total active pharmaceutical ingredient present separately in the epidermis and dermis.

In still other embodiments, the topical gel composition may be characterized by the dermal absorption or amount of drug absorbed (µg/cm$^2$), which corresponds to the amount of the naproxen (µg) present in the different skin tissues (epidermis and dermis) divided by the surface area (cm$^2$) exposed to the donor chamber. High dermal absorption is predictive of good retention of naproxen in skin tissue in vivo. The dermal absorption may be taken as the cumulative amount of drug absorbed once steady-state diffusion is achieved. The amount of drug absorbed into the epidermis, dermis and receptor may be considered individually as the sum of any combination of the epidermis, dermis, and receptor chamber. In some embodiments, the topical gel composition has a dermal absorption of naproxen into the epidermis and dermis of at least about 5 µg/cm$^2$, at least about 10 µg/cm$^2$, at least about 25 µg/cm$^2$, or at least about 50 µg/cm$^2$.

The topical gel composition may be characterized by the lag time, or the amount of time required for the active pharmaceutical ingredient to diffuse into the receptor compartment. In practical terms, the first sampling time point at which an appreciable concentration of naproxen is detectable in the receptor chamber solution may be taken as the lag time. Shorter lag times are generally indicative of faster permeation.

The topical gel composition may be alternatively characterized by a flux of naproxen into the receptor chamber (µg/cm$^2$/h). In some embodiments, the topical gel compositions as described herein have a flux of at least about 0.20 µg/cm$^2$/h, at least about 0.50 µg/cm$^2$/h, at least about 0.70 µg/cm$^2$/h, at least about 1.00 µg/cm$^2$/h, at least about 1.50 µg/cm$^2$/h, or at least about 2.00 µg/cm$^2$/h. In certain embodiments, the topical gel composition has a flux of at least about 0.20 µg/cm$^2$/h.

In other embodiments, the topical gel composition may be characterized by the relative ratios of any of the above metrics for the epidermis, dermis and receptor chamber. For example, a skin permeation/accumulation ratio may be calculated as the ratio of the dermal absorption of the epidermis to the absorption of the dermis and receptor chamber. In some embodiments, the topical gel composition has a skin permeation/accumulation ratio of between about 1:3 and about 1:1.

Appearance, Skin Aesthetics, and Evaluation

Provided herein are topical gel compositions comprising particular naproxen salts, such as naproxen ammonium, which have increased skin permeation and retention properties as well as improved skin aesthetic and sensory characteristics. In some embodiments, the present topical gel compositions comprising particular naproxen salts and combinations of the excipients described above, achieve increased therapeutic efficacy without sacrificing the smooth feel of the compositions or their transparency on patients' skin following application and subsequent drying.

In some embodiments the topical gel composition is a clear gel. In certain embodiments, the topical gel composition is a clear, colorless gel. The clarity and/or colorlessness of the topical gel compositions described herein may be evaluated by any number of tests, including but not limited to visual inspection.

In other embodiments, the topical gel composition dries clear on a patient's skin when applied. In further embodiments, the topical gel composition dries clear on a patient's skin when applied and remains transparent on the patient's skin for at least about 1 hour, at least about 3 hours, or at least about four hours after being applied. In certain embodiments, a visible white precipitate does not appear at the site of application of the topical gel composition for at least about 1 hour, at least about 3 hours, or at least about four hours after application.

Methods of Preparing Topical Gel Compositions

In another aspect, the present disclosure provides methods of preparing the topical gel compositions described herein.

As described herein, topical gel compositions comprising certain non-sodium salts of naproxen, such as naproxen ammonium and naproxen diethylammonium, have been identified to provide improved skin permeation and retention properties to the topical gel composition as compared to the naproxen sodium salt. These naproxen salts are formed in-situ with the combination of naproxen (as the free acid) with one or more neutralizing agents.

Provided herein is a method of preparing topical gel composition comprising one or more naproxen salts, comprising combining naproxen free acid with one or more neutralizing agents, a gelling agent, and water to provide the topical gel composition. In some embodiments, the method comprises combining naproxen free acid with one or more neutralizing agents, a gelling agent, water, and one or more alcoholic solvents to provide the topical gel composition. In certain embodiments of the foregoing, the method comprises combining naproxen free acid with one or more neutralizing agents, a gelling agent, water, and one or more alcoholic solvents, and optionally one or more additional excipients selected from the group consisting of a film-forming agent, an antioxidant, a preservative, and fragrance, to provide the topical gel composition.

It should be recognized that order in which the components of the topical gel composition are combined may influence the resulting physical properties of the topical gel composition. As such, the order of combination for each of the naproxen free acid, neutralizing agents and excipients may be varied to provide the desired gel composition characteristics. As one example, the gelling agent may be first combined with water to product a gel mixture, with the naproxen free acid, the one or more neutralizing agents, and additional alcoholic solvents added to the gel mixture separately or in combination.

In one aspect, the present disclosure provides a method of preparing a topical gel composition comprising:
  combining a gelling agent and water to provide a gel mixture;
  adding one or more neutralizing agents to the gel mixture;
  combining naproxen free acid, one or more alcoholic solvents, optionally a film-forming agent, and optionally an antioxidant to provide an alcohol mixture; and
  combining the alcohol mixture with the gel mixture to provide the topical gel composition.

In some embodiments of the foregoing method, the method comprises pre-heating and stirring any of the individual components or generated mixtures prior to further combining or adding. The temperatures and times for which the steps of combining and adding are performed may also be adjusted to produce the desired gel composition characteristics.

In some embodiments, the method comprises adding one or more neutralizing agents to the gel mixture, wherein the one or more neutralizing agents comprises ammonia solution (ammonium hydroxide), triethanolamine, diethylamine, potassium hydroxide, or any combinations thereof. In other embodiments, the method comprises adding ammonia solution to the gel mixture.

It should be recognized that, depending upon the desired concentration of the naproxen salt in the final formulation, the quantities of the naproxen and neutralizing agent(s) used to prepare the topical gel composition may be adjusted accordingly. In some embodiments, the neutralizing agent(s) and the naproxen free acid are combined in a 1:1 stoichiometric molar ratio.

In some embodiments, the method comprises combining naproxen free acid with ammonia solution, a gelling agent, and water to provide the topical gel composition, wherein the topical gel composition comprises naproxen ammonium. In other embodiments, the method comprises combining naproxen free acid with triethanolamine, a gelling agent, and water to provide the topical gel composition, wherein the topical gel composition comprises naproxen triethanolammonium. In yet other embodiments, the method comprises combining naproxen free acid with diethylamine, a gelling agent, and water to provide the topical gel composition, wherein the topical gel composition comprises naproxen diethylammonium. In still other embodiments, the method comprises combining naproxen free acid with potassium hydroxide, a gelling agent, and water to provide the topical gel composition, wherein the topical gel composition comprises naproxen potassium.

In some embodiments of the method, the quantity of the one or more neutralizing agents added to the gel mixture is greater than or equal to one molar equivalent of the naproxen free acid. In certain embodiments, the quantity of the ammonia solution is greater than or equal to one molar equivalent of the quantity of the naproxen free acid. In certain embodiments, the quantity of the one or more neutralizing agents added to the gel mixture is such that the final topical gel composition has a pH of less than or equal to pH 9 or less than or equal to pH 8.

In other embodiments, the one or more alcoholic solvents comprise ethanol, propylene glycol, polyethylene glycol, or any combinations thereof. In certain embodiments, the one or more alcoholic solvents comprise ethanol and propylene glycol. In other embodiments, the one or more alcoholic solvents comprise ethanol and polyethylene glycol. In yet other embodiments, the one or more alcoholic solvents comprise ethanol, propylene glycol, and polyethylene glycol.

Methods of Use

In another aspect, the present disclosure also provides methods of treating pain, comprising administering the topical gel compositions as described herein to a patient in need thereof. The topical gel compositions of the present disclosure achieve improved skin permeation and skin retention through the use of particular naproxen salts, such as naproxen ammonium, for localized pain relief with enhanced therapeutic efficacy. As such, the topical gel compositions described herein are especially suitable to treat superficial or deep somatic pain, such as pains and aches in muscles and joints, and may be applied directly to the site of pain. In some embodiments, provided herein is a method of treating aches and pains associated with muscles and joints.

In some embodiments, the present disclosure provides for a method of treating muscle pain or joint pain, comprising topically administering a topical gel composition comprising particular naproxen salts, to a patient in need thereof. In certain embodiments, the present disclosure provides a method of treating muscle pain or joint pain, comprising topically administering a topical gel composition comprising naproxen ammonium, to a patient in need thereof.

In some embodiments, provided herein is a method of treating muscle pain or joint pain in a patient in need thereof, comprising applying a topical gel composition comprising naproxen ammonium to the patient's skin at the site of pain.

The topical gel compositions described herein may be especially suitable for the treatment of aches and pains associated with particular conditions and/or injuries that are amenable to topical treatment. For example, in certain embodiments, the muscle pain or joint pain is associated with arthritis, sprains, strains, bruises, or backache. In some embodiments the muscle or joint pain is associated with arthritis. In certain embodiments, provided herein is a method of treating aches and pains associated with osteoarthritis.

In some embodiments of the foregoing method, the topical gel composition remains transparent on the patient's skin at the site of application for at least about 1 hour, at least about 3 hours, or at least about four hours after application. In some embodiments of the foregoing method, the topical gel composition remains transparent on the patient's skin for at least four hours following application. In certain embodiments, a visible white residue does not appear at the site of application of the topical gel composition for at least about 1 hour, at least about 3 hours, or at least about four hours after application.

ENUMERATED EMBODIMENTS

The following enumerated embodiments are representative of some aspects of the present disclosure.

1. A topical gel composition, comprising:
   naproxen ammonium;
   one or more gelling agents; and
   water.
2. The topical gel composition of embodiment 1, wherein the topical gel composition has a total concentration of naproxen of at least 1% w/w.
3. The topical gel composition of embodiment 1 or embodiment 2, wherein the topical gel composition has a total concentration of naproxen between 1% w/w and 20% w/w.
4. The topical gel composition of any one of embodiments 1 to 3, wherein the topical gel composition comprises at least about 25% w/w water.
5. The topical gel composition of any one of embodiments 1 to 4, wherein the topical gel composition comprises at least 1.0% w/w one or more gelling agents.
6. The topical gel composition of any one of embodiments 1 to 5, wherein the one or more gelling agents comprise hydroxyethylcellulose.
7. The topical gel composition of any one of embodiments 1 to 6, wherein the topical gel composition comprises one or more alcoholic solvents selected from the group consisting of ethanol, propylene glycol, polyethylene glycol, and any combinations thereof.
8. The topical gel composition of any one of embodiments 1 to 7, wherein the topical gel composition comprises ethanol.
9. The topical gel composition of any one of embodiments 1 to 8, wherein the topical gel comprises at least 30% w/w ethanol.
10. The topical gel composition of any one of embodiments 1 to 9, wherein the topical gel composition comprises propylene glycol.
11. The topical gel composition of any one of embodiments 1 to 10, wherein the topical gel composition comprises between 1% w/w and 10% w/w propylene glycol.
12. The topical gel composition of any one of embodiments 1 to 11, wherein the topical gel composition comprises polyethylene glycol.
13. The topical gel composition of any one of embodiments 1 to 12, wherein the topical gel composition comprises between 2.5% w/w and 20% w/w polyethylene glycol.
14. The topical gel composition of any one of embodiments 1 to 13, wherein the topical gel composition comprises propylene glycol and polyethylene glycol.
15. The topical gel composition of any one of embodiments 1 to 14, wherein the topical gel composition comprises between 5% w/w and 20% w/w of a combination of propylene glycol and polyethylene glycol.
16. The topical gel composition of any one of embodiments 1 to 15, wherein the topical gel composition further comprises one or more pharmaceutically acceptable excipients selected from the group consisting of one or more antioxidants, one or more preservatives, one or more sensates, and fragrance.
17. The topical gel composition of any one of embodiments 1 to 16, wherein the topical gel composition further comprises between 0.1% w/w and 0.25% w/w sodium metabisulfite.
18. The topical gel composition of any one of embodiments 1 to 17, wherein the topical gel composition further comprises between 0.1% w/w and 0.20% w/w EDTA.
19. The topical gel composition of any one of embodiments 1 to 18, wherein the topical gel composition further comprises between 0.1% w/w and 1.0% w/w glycerin.
20. The topical gel composition of any one of embodiments 1 to 19, wherein the topical gel composition comprises one or more film-forming agents.
21. The topical gel composition of any one of embodiments 1 to 20, wherein the topical gel composition comprises copovidone.
22. The topical gel composition of any one of embodiments 1 to 21, wherein the topical gel composition has a pH of between pH 7 and pH 9.
23. The topical gel composition of any one of embodiments 1 to 22, wherein the topical gel composition has a viscosity of between 7,000 cP and 11,000 cP.
24. The topical gel composition of any one of embodiments 1 to 23, wherein the topical gel composition is a clear gel.
25. The topical gel composition of any one of embodiments 1 to 24, wherein the topical gel composition has a dermal absorption of naproxen into the epidermis and dermis of at least 5 μg/cm$^2$ as determined by an in vitro permeation test.
26. The topical gel composition of any one of embodiments 1 to 25, wherein the topical gel composition has a flux of at least 0.20 μg/cm$^2$/h as determined by an in vitro permeation test.
27. The topical gel composition of any one of embodiments 1 to 26, wherein the topical gel composition has a flux of between 0.20 μg/cm$^2$/h and 2.00 μg/cm$^2$/h as determined by an in vitro permeation test.
28. The topical gel composition of any one of embodiments 1 to 27, wherein the topical gel composition has a skin permeation/accumulation ratio of between 1:3 and 1:1.
29. A method of treating muscle pain or joint pain in a patient in need thereof, comprising applying a topical gel composition according to any one of embodiments 1 to 28, to the patient's skin at the site of pain.
30. The method of embodiment 29, wherein the muscle pain or joint pain is associated with arthritis, sprains, strains, bruises, or backache.

31. The method of embodiment 29 or embodiment 30, wherein the topical gel composition remains transparent on the patient's skin for at least 1 hour after application.

32. The method of any one of embodiments 29 to 31, wherein the topical gel composition remains transparent on the patient's skin at least four hours after application.

33. A method of preparing the topical gel composition of any one of embodiments 1 to 28, comprising:

combining a gelling agent and water to provide a gel mixture;

adding ammonia solution to the gel mixture;

combining naproxen free acid, one or more alcoholic solvents, optionally a film-forming agent, and optionally an antioxidant to provide an alcohol mixture; and combining the alcohol mixture with the gel mixture to provide the topical gel composition.

34. The method of embodiment 33, wherein the quantity of the ammonia solution is greater than or equal to one molar equivalent of the quantity the naproxen free acid.

35. The method of embodiment 33 or embodiment 34, wherein the one or more alcoholic solvents comprises ethanol, propylene glycol, polyethylene glycol, or any combinations thereof.

EXAMPLES

Example 1: Neutralizing Agent (In Situ Salt) Comparison

In vitro permeation tests (IVPT) were conducted using different topical gel compositions of naproxen in combination with various neutralizing agents to evaluate their skin permeation and skin retention characteristics.

Sample Preparation. Table 1 shows the formulations of the different clear, aqueous gel samples containing naproxen in combination with various neutralizing agents—triethanolamine (Nap+TEA), diethylamine (Nap+Et$_2$NH), a 28-30% ammonia solution (Nap+NH$_3$)—and naproxen sodium salt (Nap+Na), prepared for IVPT evaluation. For the naproxen sodium salt formulation, no neutralizing agent was added to the gel mixture and naproxen sodium salt was utilized in lieu of naproxen for preparation of the active ingredient solution.

TABLE 1

| | Sample | | | |
|---|---|---|---|---|
| Active Ingredient | Naproxen sodium 11.0% w/w | Naproxen 10.0% w/w | Naproxen 10.0% w/w | Naproxen 10.0% w/w |
| Neutralizing Agent | — | Triethanolamine (TEA) 8.40% w/w | Diethylamine (Et$_2$NH) 3.20% w/w | Ammonia solution (NH$_3$) 2.80% w/w |
| Gelling Agent | HEC H grade 1.4% w/w | | | |
| Solvent | Propylene glycol 10.0% w/w | | | |
| Solvent | Ethanol 30.0% w/w | | | |
| Antioxidant | Sodium metabisulfite 0.10% | | | |
| Purified Water | Q.S. to 100% | | | |

In vitro Permeation Tests. The four samples prepared in Table 1 were used in in vitro permeation tests (IVPT) in a Franz diffusion cell to determine the effect of neutralizing agents on the skin permeation and retention properties of naproxen in the formulations. For the IVPT, a vertical Franz diffusion cell was employed, using frozen, excised human skin (300-500 µm thickness) as the permeable membrane for each experiment. The receptor chamber was filled with 1×PBS buffer (5 mL, pH 7.4) sonicated to remove any dissolved gases. During the permeation tests, the receptor compartment buffer was stirred continuously at 600 rpm throughout and maintained at a temperature of 32° C. The skin membrane was mounted with the stratum corneum facing up (donor side), exposed to air at room temperature to simulate in vivo application. Sample formulations were applied (6.4 mg, 0.64 cm$^2$) to the donor side of the skin membrane via positive displacement pipette.

The diffusion of naproxen was monitored via the sample port connected to the receptor chamber of the diffusion cell at the following time points: 0 h, 3 h, 6 h, 12 h, 22 h, and 24 h. At each time interval, 300 µL aliquots of the buffer solution were taken and analyzed by HPLC for naproxen concentration. After the final 24 h time point, excess unabsorbed formulation was wiped from the surface of the skin membrane. The excised skin membrane was separated into the epidermis and dermis layers using forceps.

The epidermal layer was minced manually using surgical scissors for individual analysis. Methanol (3 mL) was added to the minced epidermis and shaken for 4 h to extract naproxen. The extract solution was filtered with a 0.45 µm Millipore membrane nylon filter and analyzed by HPLC. It is noted that the epidermal layer in these studies included the stratum corneum layer, due to non-negligible removal of the epidermal layer with the stratum corneum under standard tape stripping procedures. The dermis was prepared and analyzed for naproxen content as described for the epidermal layer above.

For the HPLC analysis, the following parameters were utilized—Mobile Phase: Acetonitrile (70%), water with 0.1% TFA (30%); Flow rate: 1.0 mL/min; Run time: 7 min; Retention time: ~4 min; Column: (size and particle size): Luna 5u C892) 100 A LC Column 250×4.6 mm; Column Temperature: 25° C.; Detection Wavelength: 272 nm.

For each formulation, the in vitro permeation tests were conducted using six cells (n=6). A commercially available topical naproxen gel composition (Naprosyn®) was included as a reference sample alongside the formulated samples.

Figure 1B:
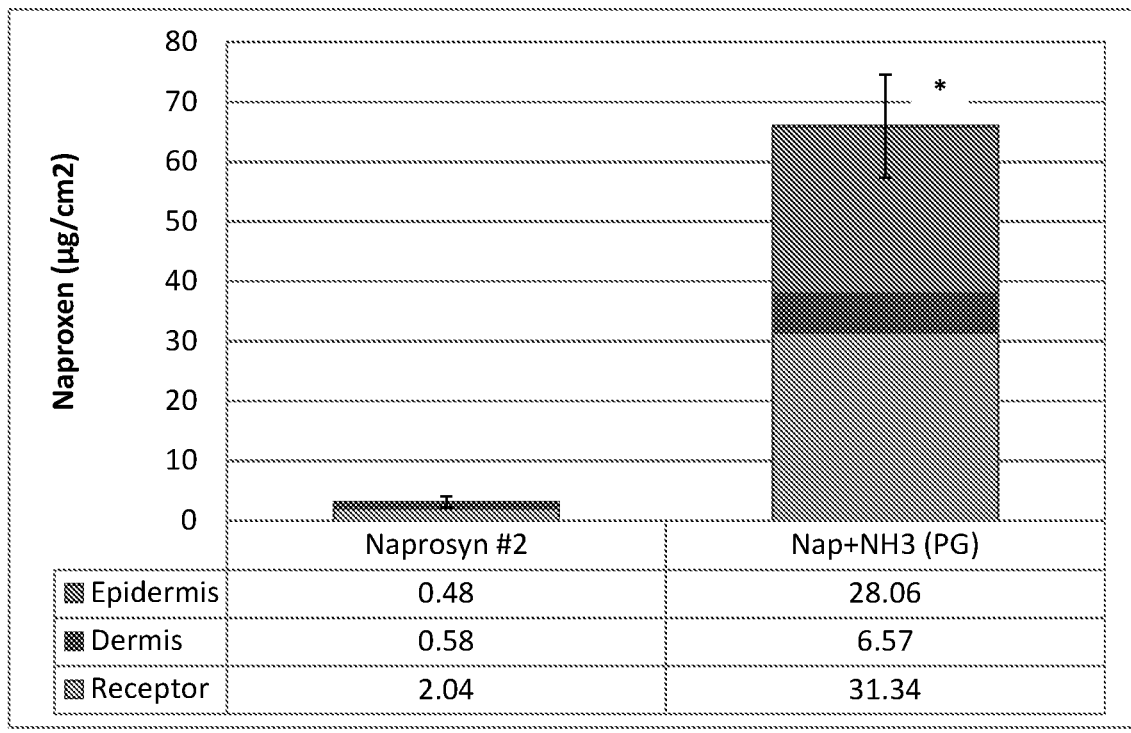

Table 2 shows the skin permeation and retention results of the IVPT studies, including the distribution of naproxen across the epidermis, dermis and receptor chamber, the dermal absorption and flux after 24 hours for each of the sample formulations. The percent recovery ranged from 89 to 113%. FIGS. 1A and 1B show the permeation of naproxen into the receptor compartment and skin distribution profiles (epidermis and dermis) for different salt formulations prepared in Tables 1 and 2 as compared to commercially available Naprosyn® topical gel (10% w/w). The standard deviations for the total amount of drug absorbed (µg/cm$^2$) (the sum of the receptor, epidermis and dermis) are shown for each formulation in FIGS. 1A and 1B, where measured.

It was observed that the formulations containing diethylamine and ammonia solution as neutralizing agents showed significant increases in the dermal absorption of naproxen as compared to the Naprosyn® reference sample and the samples containing naproxen sodium salt and naproxen with triethanolamine as the neutralizing agents—suggesting both an increase in skin permeation and skin retention for the diethylamine (Et$_2$NH) and ammonia (NH$_3$) samples.

TABLE 2

| Parameters | Naprosyn #1 | Naprosyn #2 | Naproxen sodium (11.0% w/w) | Naproxen (10% w/w) + KOH | + TEA | + Et₂NH | + NH₃ #1 |
|---|---|---|---|---|---|---|---|
| Epidermis ($\mu g/cm^2$) | 0.89 | 0.48 | 1.34 | 0.00 | 0.87 | 8.74 | 28.06 |
| Dermis ($\mu g/cm^2$) | 0.51 | 0.58 | 0.27 | 0.00 | 1.18 | 2.34 | 6.57 |
| Receptor ($\mu g/cm^2$) | 1.94 | 2.04 | 2.11 | 2.92 | 1.95 | 33.53 | 31.34 |
| Amount of Drug Absorbed ($\mu g/cm^2$) | 3.34 ± 0.71 | 3.10 ± 0.92 | 3.72 ± 0.63 | 2.92 ± 0.35 | 4.00 ± 0.94 | 44.61 ± 2.59 | 65.97 ± 8.66 |
| Flux ($\mu g/cm^2/hr$) | 0.09 | 0.10 | 0.09 | 0.09 | 0.09 | 2.07 | 2.06 |

Skin Aesthetics Evaluation. The prepared formulations containing naproxen in combination with various neutralizing agents were also assessed for skin aesthetics. An additional sample containing potassium hydroxide as a neutralizing agent was prepared according to the protocol and base formulations above for aesthetic evaluation.

Each sample was applied to the hand of a human subject and allowed to dry. Four hours after application, the skin aesthetics of each formulation were assessed visually for the appearance of any residue. Table 3 shows the results of the aesthetic assessment. All sample formulations, with the exception of the potassium hydroxide formulation, exhibited precipitation of a white residue after four hours. However, the potassium hydroxide formulation exhibited low accumulation in the epidermis and dermis in in vitro diffusion studies as shown in Table 2.

TABLE 3

| Active Ingredient | Naproxen sodium 11.0% w/w | Naproxen 10.0% w/w | Naproxen 10.0% w/w | Naproxen 10.0% w/w | Naproxen 10.0% w/w |
|---|---|---|---|---|---|
| Neutralizing Agent | — | TEA 8.4% w/w | Diethylamine 3.20% w/w | Ammonia solution 2.80% w/w | KOH 2.45% w/w |
| Solvent | | | Propylene glycol 10.0% w/w | | |
| Solvent | | | Ethanol 30.0% w/w | | |
| Residue on skin | White | White | White | White | None |

Example 2: Excipient Effects on Skin Aesthetics

In order to assess the effect of different excipients, in particular the solvent combinations, on the final appearance of the topical gel composition on the skin, as well as the permeation and retention properties, additional sample formulations containing polyethylene glycol as a substitute for or in combination with propylene glycol were evaluated by IVPT.

Part I: Polyethylene Glycol as Solvent.

Figure 2:
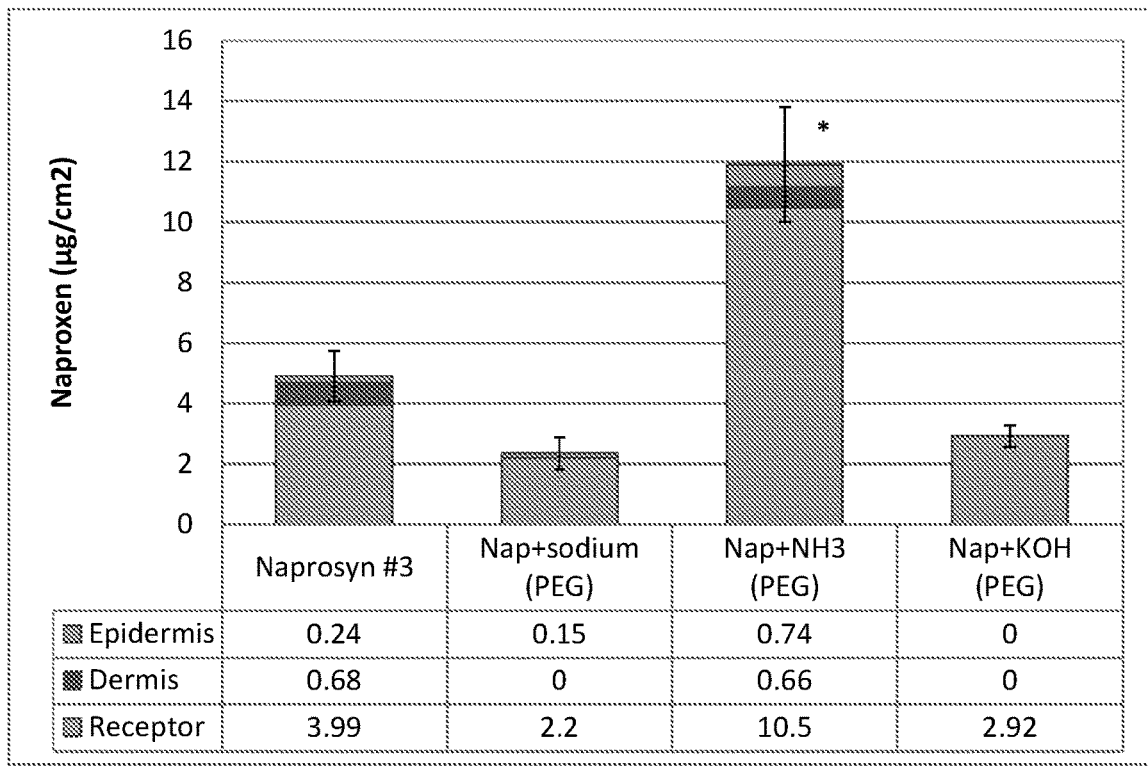
FIG. 2 depicts the skin distribution profiles (epidermis and dermis) and receptor chamber permeation of naproxen (in $\mu g/cm^2$) of different topical gel formulations of naproxen in combination with various neutralizing agents using polyethylene glycol (PEG 400) as a solvent observed in IVPT using a Franz diffusion cell. Naprosyn® topical gel was also evaluated. Statistically significant differences between the different formulations have been denoted by an asterisk in the figure.

Sample formulations containing naproxen sodium, naproxen and ammonia solution, and naproxen with potassium hydroxide were prepared as described in Example 1 with polyethylene glycol (PEG 400) used in lieu of propylene glycol as a solvent. Table 4 shows the components for each of the formulations prepared. The sample formulations were evaluated by in vitro permeation tests for skin permeation and retention attributes, as well as aesthetic appearance, using the same protocols as described in Example 1. FIG. 2 shows the observed dermal absorption and Table 5 provides the results for the skin aesthetics assessment for the sample formulations prepared herein. The standard deviations for the total amount of drug absorbed ($\mu g/cm^2$) (the sum of the receptor, epidermis and dermis) are shown for each formulation, where measured, in FIG. 2.

TABLE 4

| | Sample | | |
|---|---|---|---|
| Active Ingredient | Naproxen sodium 11.0% w/w | Naproxen 10.0% w/w | Naproxen 10.0% w/w |
| Neutralizing Agent | — | Ammonia solution 2.80% w/w | KOH 2.45% w/w |
| Gelling Agent | | HEC H grade 1.4% w/w | |
| Solvent | | PEG 400 10.0% w/w | |
| Solvent | | Ethanol 30.0% w/w | |
| Antioxidant | | Sodium metabisulfite 0.10% | |
| Purified Water | | Q.S. to 100% | |

TABLE 5

| | Sample | | |
|---|---|---|---|
| Active Ingredient | Naproxen sodium 11.0% w/w | Naproxen 10.0% w/w | Naproxen 10.0% w/w |
| Neutralizing Agent | — | Ammonia solution 2.80% w/w | KOH 2.45% w/w |
| Solvent | | PEG 400 10.0% w/w | |
| Solvent | | Ethanol 30.0% w/w | |
| Residue on skin | None | Barely noticeable white | None |

Figure 3:
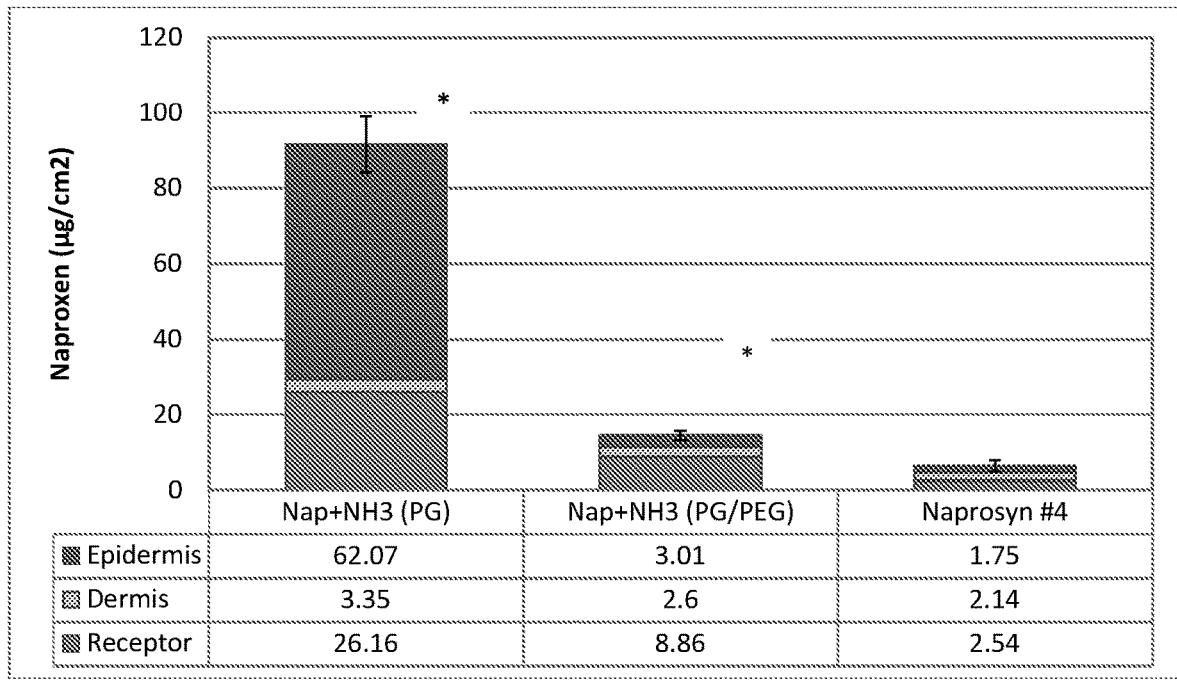
FIG. 3 depicts skin distribution profiles (epidermis and dermis) and receptor chamber permeation of naproxen (in $\mu g/cm^2$) in topical gel formulations using ammonia solution as a neutralizing agent with propylene glycol, and propylene glycol with polyethylene glycol as solvent(s) observed in IVPT using a Franz diffusion cell. Naprosyn® topical gel was also evaluated. Statistically significant differences between the different formulations have been denoted by an asterisk in the figure.
Figure 4:
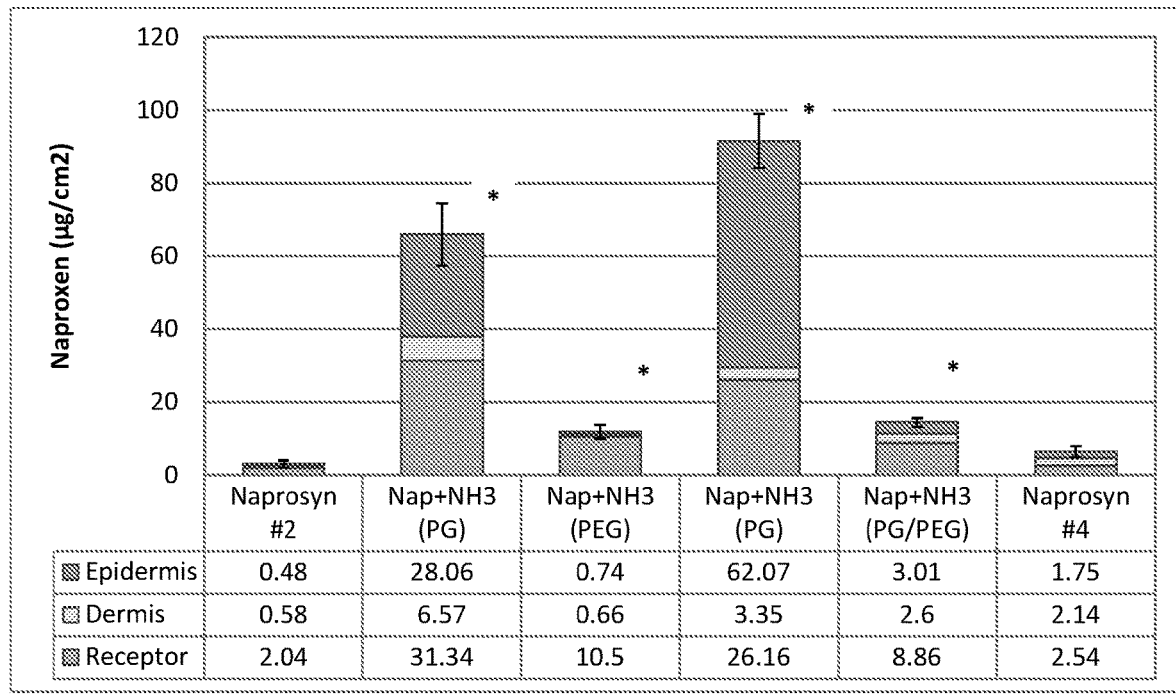
FIG. 4 depicts skin distribution profiles (epidermis and dermis) and receptor chamber permeation of naproxen (in $\mu g/cm^2$) in different topical gel formulations of naproxen with ammonia solution using different solvents observed in IVPT using a Franz diffusion cell. Naprosyn® topical gel was also evaluated. Statistically significant differences between the different formulations have been denoted by an asterisk in the figure.
Figure 5:
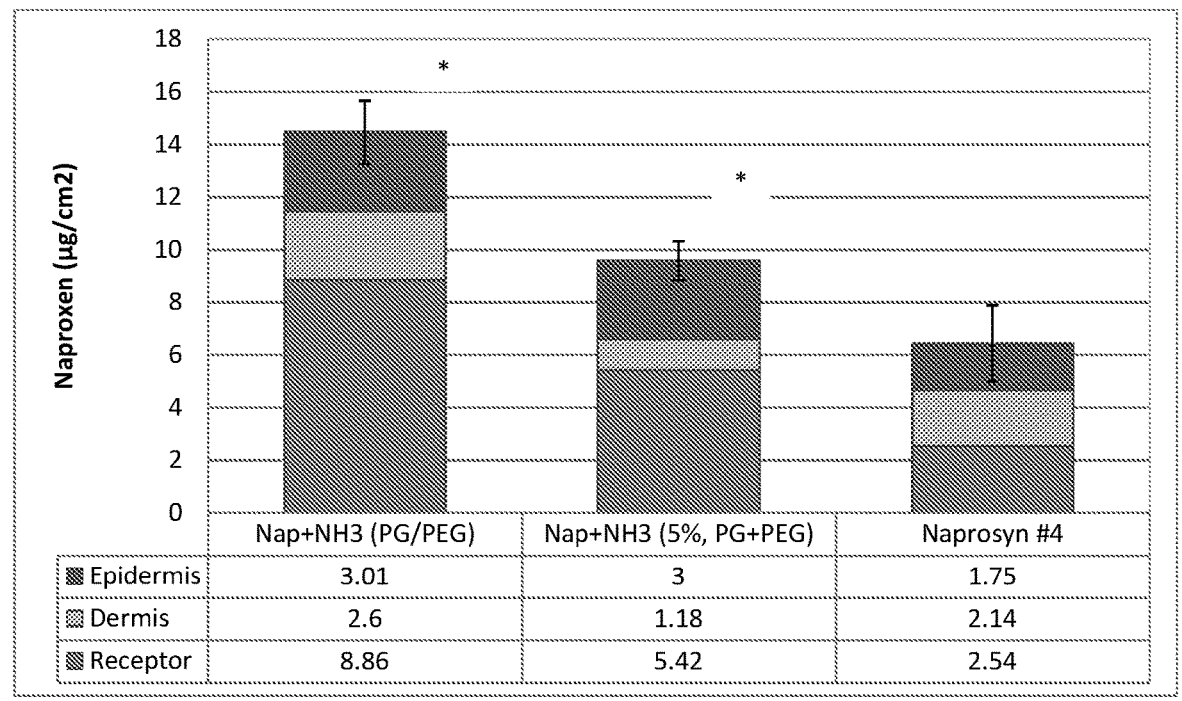
FIG. 5 depicts skin distribution profiles of naproxen (epidermis and dermis) and receptor chamber permeation of naproxen (in $\mu g/cm^2$) for formulations containing 10% w/w and 5% w/w naproxen, using ammonia solution as a neutralizing agent with propylene glycol with polyethylene glycol as solvents observed in IVPT using a Franz diffusion cell. Naprosyn® topical gel was also evaluated. Statistically significant differences between the different formulations have been denoted by an asterisk in the figure.

Tables 6 and 7 provide dermal absorption data from IVPT assessment for Naprosyn®, naproxen sodium salt formulations with propylene glycol or polyethylene glycol as solvent, and naproxen in combination with ammonia solution as a neutralizing agent and propylene glycol or polyethylene glycol as a solvent. The in vitro permeation data for the formulations containing propylene glycol were taken from Example 1.

ethylene glycol (Nap+NH$_3$ (PEG)), and with propylene glycol and polyethylene glycol (Nap+NH$_3$ (PG+PEG)). Table 9, FIG. 3, FIG. 4 and FIG. 5 show the results of the in vitro permeation tests for each of the ammonia solution

TABLE 6

| | Sample | | | | |
|---|---|---|---|---|---|
| Parameters | Naprosyn (10% naproxen) #3 | Naproxen sodium (11.0% w/w) | Naproxen sodium (11.0% w/w) | Naproxen (10.0% w/w) + NH$_3$ #1 | Naproxen (10.0% w/w) + NH$_3$ |
| Solvent | — | Propylene glycol 10.0% w/w | PEG 400 10.0% w/w | Propylene glycol 10.0% w/w | PEG 400 10.0% w/w |
| Epidermis (µg/cm$^2$) | 0.24 | 1.34 | 0.15 | 28.06 | 0.74 |
| Dermis (µg/cm$^2$) | 0.68 | 0.27 | 0 | 6.57 | 0.66 |
| Receptor (µg/cm$^2$) | 3.99 | 2.11 | 2.2 | 31.34 | 10.5 |
| Amount of Drug Absorbed (µg/cm$^2$) | 4.91 ± 0.85 | 3.72 ± 0.63 | 2.35 ± 0.52 | 65.97 ± 8.66 | 11.91 ± 1.89 |
| Flux (µg/cm$^2$/hr) | 0.09 | 0.09 | 0.09 | 2.06 | 0.09 |

TABLE 7

| Sample | Active Ingredient | Neutralizing Agent | Propylene glycol 10.0% w/w | PEG 400 10.0% w/w |
|---|---|---|---|---|
| Nap + sodium | Naproxen sodium 11.0% w/w | — | 1.61 µg/cm$^2$ (43%) | 0.15 µg/cm$^2$ (52%) |
| Nap + NH$_3$ | Naproxen 10.0% w/w | Ammonia solution 2.80% w/w | 34.63 µg/cm$^2$ (52%) | 1.40 µg/cm$^2$ (12%) |

It was observed that the use of polyethylene glycol in place of propylene glycol was useful to reduce the formation of residual precipitate after application and drying, however, also resulted in substantial decrease in dermal absorption of naproxen overall.

Part II. Propylene Glycol and Polyethylene Glycol as Co-Solvents.

Based on the results of the Example 1 and Part I of Example 2 above, an additional sample formulation of naproxen with ammonia solution as neutralizing agent was prepared to include both propylene glycol and polyethylene glycol as co-solvents to determine whether the enhancement of dermal absorption and desired skin aesthetics (transparent drying) could be achieved simultaneously.

A sample formulation of naproxen with ammonia solution as a neutralizing agent was prepared according to the protocol described in Example 1 above, but with propylene glycol and polyethylene glycol as solvents and with an added film-forming agent copovidone. The sample formulation was evaluated for its skin permeation and retention characteristics and for skin aesthetics according to the protocols for in vitro permeation tests and visual assessment outlined in Example 1. Table 8 shows the compositional elements of the formulation comprising both propylene glycol and polyethylene glycol as solvents as compared to the previously tested formulations of naproxen with ammonia solution from Example 1 and Example 2, Part I. Table 8 also provides the results of the visual assessment for each of the ammonia solution samples—naproxen and ammonia solution with propylene glycol (Nap+NH$_3$ (PG)), with polysamples. In Table 9, the formulation containing only propylene glycol (#2) was a replicate preparation and measurement of the propylene glycol-only formulation (#1) in Table 6. The standard deviations for the total amount of drug absorbed (µg/cm$^2$) (the sum of the receptor, epidermis and dermis) are shown for each formulation, where measured, in FIG. 3, FIG. 4 and FIG. 5.

TABLE 8

| | Sample | | |
|---|---|---|---|
| | Naproxen | Naproxen | Naproxen |
| Active Ingredient | 10.0% w/w | 10.0% w/w | 10.0% w/w |
| Neutralizing Agent | | Ammonia solution 2.80% w/w | |
| Solvent | Propylene Glycol 10.0% w/w | — | Propylene Glycol 10.0% w/w |
| Solvent | — | PEG 400 10.0% w/w | PEG 400 10.0% w/w |
| Film-Forming Agent | — | — | Copovidone 1.0% w/w |
| Solvent | | Ethanol 30.0% w/w | |
| Residue on skin | White | Barely noticeable White | Barely noticeable White |

The sample formulation containing both propylene glycol and polyethylene glycol as co-solvents demonstrated a significant reduction in white residue observed as compared to the sample containing propylene glycol alone but was similar in appearance to the sample containing polyethylene glycol alone. In vitro permeation evaluation of the sample with the solvent combination of propylene glycol and polyethylene demonstrated reduced dermal absorption relative to the sample containing propylene glycol alone but enhancement of skin retention as compared to the formulation containing only polyethylene glycol.

TABLE 9

| Parameters | Sample | | | | |
|---|---|---|---|---|---|
| | Naprosyn (10.0% naproxen) #4 | Naproxen (10.0% w/w) + ammonia solution #2 | Naproxen (10.0% w/w) + ammonia solution | Naproxen (10.0% w/w) + ammonia solution | Naproxen (5% w/w) + ammonia solution |
| Solvent | — | Propylene glycol 10% w/w | PEG 400 10% w/w | Propylene glycol 10% w/w + PEG 400 10% w/w | Propylene glycol 10% w/w + PEG 400 10% w/w |
| Epidermis ($\mu g/cm^2$) | 1.75 | 62.07 | 0.74 | 3.01 | 3.00 |
| Dermis ($\mu g/cm^2$) | 2.14 | 3.35 | 0.66 | 2.6 | 1.18 |
| Receptor ($\mu g/cm^2$) | 2.54 | 26.16 | 10.5 | 8.86 | 5.42 |
| Amount of Drug Absorbed ($\mu g/cm^2$) | 6.43 ± 1.45 | 91.58 ± 7.40 | 11.91 ± 1.89 | 14.47 ± 1.20 | 9.60 ± 0.74 |
| Flux ($\mu g/cm^2/hr$) | 0.09 | 1.45 | 0.09 | 0.38 | 0.23 |

Example 3: In Vivo Evaluation: Rat Paw Test

The example below was conducted to evaluate the effect of various naproxen ammonium topical gel formulations (Table 10) on inflammation/edema induced by carrageenan-injection into the footpads of Sprague Dawley (SD) rats. In addition, the effects for commercially available (control) topical analgesic formulations including Naprosyn® Gel, Momendol Gel (naproxen), and Voltaren® Gel (diclofenac), as well as naproxen administered orally, were evaluated. The topical formulations shown in Table 10 below were applied to the respective animal subject three (3) hours—or one (1) hour in the case of the oral controls—prior to the carrageenan injection to induce swelling. Efficacy evaluation was based on gait analysis, von Frey absolute thresholds and ankle caliper differentials recorded over 24 h after initial carrageenan injection, and paw differential weights following euthanasia of the test subjects. Table 11 shows the compositions of the naproxen ammonium topical gel test formulations utilized for the treatment groups in Table 10.

TABLE 10

| Group | N | Treatment | Dose Level (mg/kg oral, or mg/rat topical) | Dose Route | Dose Volume (mg/kg oral, or μl/rat topical) | Dose Conc. (mg/ml oral, or % topical) |
|---|---|---|---|---|---|---|
| 1 | 10 | Oral vehicle (1% CMC/0.05% Tween® 80) | 0 | PO | 2 mg | 0 mg |
| 2 | 10 | Naproxen | 25 | PO | 2 mg | 12.5 mg |
| 3 | 10 | Topical Vehicle (control) (Am/10% PG) | 0 mg | TOP | 100 μL | 0% |
| 4 | 10 | Topical Vehicle (control) (Am/10% PG/10% PEG/copovidone) | 0 mg | TOP | 100 μL | 0% |
| 5 | 10 | Diclofenac Gel (Voltaren®) | 2.32 mg | TOP | 100 μL | 2.32% |
| 6 | 10 | Naprosyn® Gel | 10 mg | TOP | 100 μL | 10.0% |
| 7 | 10 | Momendol Gel | 10 mg | TOP | 100 μL | 10.0% |
| 8 | 10 | Naproxen Topical Gel, 10% w/w (Am/10% PG) | 10 mg | TOP | 100 μL | 10.0% |
| 9 | 10 | Naproxen Topical Gel, 10% w/w (Am/10% PG/10% PEG/copovidone) | 10 mg | TOP | 100 μL | 10.0% |
| 10 | 10 | Naproxen Topical Gel, 10% w/w (Am/10% PG) | 5 mg | TOP | 100 μL | 5.0% |
| 11 | 10 | Naproxen Topical Gel, 10% w/w (Am/10% PG) | 1 mg | TOP | 100 μL | 1.0% |

CMC = carboxymethylcellulose

TABLE 11

| Functional Ingredient | Treatment Group # | | | | | |
|---|---|---|---|---|---|---|
| | #3 | #4 | #8 | #9 | #10 | #11 |
| Naproxen (% w/w) | 0% | 0% | 10.0% | 10% | 5.0% | 1.0% |
| Neutralizing Agent (% w/w) | 0.00% | 0.00% | Ammonia solution 2.80% | 2.80% | 1.40% | 0.30% |
| Gelling Agent | HEC H grade, 1.4% w/w | | | | | |
| Propylene Glycol (% w/w) | 10.0% | 10.0% | 10.0% | 10.0% | 10.0% | 10.0% |
| PEG 400 (% w/w) | 0% | 10.0% | 0% | 10.0% | 0% | 0% |
| Ethanol (% w/w) | 30.0% | 30.0% | 30.0% | 30.0% | 30.0% | 30.0% |
| Copovidone (% w/w) | 0% | 1.0% | 0% | 1.0% | 0% | 0% |
| Sodium metabisulfite | 0.10% | 0.10% | 0.10% | 0.10% | 0.10% | 0.1% |
| Purified Water | Q.S. to 100% | | | | | |

Experimental Design. Male Sprague Dawley (Envigo RMS, Inc., Indianapolis) were weighed on Day 1 (mean 285 g) and randomized by body weight into treatment groups. On Day 0-1, animals in Groups 3-11 were dosed with topical compounds on 2-minute intervals according to the dose schedules in Table 10. Two hours later, animals in Groups 1-2 were dosed orally with test articles as indicated in Table 10. One hour (for oral) or three hours (for topical) post-treatment, the animals were anesthetized and injected with carrageenan into the right hind paw. Gait and von Frey analyses were conducted at time points of 2 h, 4 h, 6 h, 8 h, and 24 h post-carrageenan injection; ankle caliper measurements were taken immediately following gait assessment. Following conclusion of the live phase at 24-h post-carrageenan injection and completion of Von Frey analysis and ankle caliper measurements, the animals were immediately euthanized and hind paws were collected and weighed.

Gait Analysis. Gait analysis was performed prior to carrageenan injection (T=0 h, baseline), and again at 2 h, 4 h, 6 h, 8 h, and 24 h post-carrageenan injection, by applying ink to the ventral surface of the foot and documenting weight bearing during movements (footprints) across paper. Rear feet of rats were placed in ink, then rats were placed on paper and allowed to walk the full length. This process was repeated as necessary to generate 4 clear, evenly inked footprint pairs representing the overall pattern of gait. Gait was scored visually as follows (descriptions refer to diseased leg):

0=Normal, approximately equal ink staining to normal paw.
1=Slight limp/pain. Reduced inking area relative to the normal paw, but no full regions or structures are missing.
2=Mild limp/pain. Print extends to the end or near to the end of the "curlicue" structure. If normal paw has very little heel staining (rat walks mainly on toes/ball of foot), then slightly less staining.
3=Moderate limp/pain. Toes and full ball of foot, extending to the top of the "curlicue" structure are present. If normal paw has very little heel staining (rat walks mainly on toes/ball of foot), then toes with small portion of ball of foot.
4=Marked limp/pain. Toes and partial ball of foot, no heel or posterior foot. If normal paw has very little heel staining (rat walks mainly on toes/ball of foot), then toes only.
5=Severe limp/pain. Toes only, no ball of foot, no heel. If normal paw has very little heel staining (rat walks mainly on toes/ball of foot), then partial toes or non-specific marks.
6=Hopping. Carrying leg, no footprint is evident.

Von Frey Analysis. Von Frey analysis was performed on the right hind paw prior to carrageenan injection (T=0 h, baseline), and again at 2 h, 4 h, 6 h, 8 h, and 24 h post-carrageenan injection. Test groups were blinded to researchers during testing Rats were habituated to the animal colony for one week and handled four times for five minutes each after the week of habituation. Animals were also habituated to the von Frey testing rack three times during this process. The von Frey testing kit used for the analysis consisted of a set of hairs ranging from 3.16 to 5.18 g absolute threshold for rats. The same kit was utilized throughout to avoid variability among kits.

Testing began with three applications of the 4.31 hair. A response was recorded if the animal had an obvious reaction to the hair, typically manifested as lifting of the hind paw from the grate to relieve the pressure. Responses were recorded as either a 0 (no response) or a 1 (response). If the animal did not respond to the hair three times in a row, the next larger hair in the kit was applied and the process was repeated until the animal responded three times in a row. Following the response, the previous filament was retested to confirm lack of response. If the animal did respond, the next smaller filament was applied and the process was repeated until the animal no longer responded. Once a lack of response was observed, the previous filament was retested to confirm the response.

Testing was done on hind (heel) portions of the hind paw. Testers monitored the animals for hyper-responding or freezing, in which case animals were left alone until calm. A fitting program was used to calculate a 50% response threshold based upon the 100% response rates observed during testing.

Ankle Caliper Measurement. Caliper measures of right and left ankle diameters were taken prior to carrageenan injection (T=0 h, baseline), and again at 2 h, 4 h, 6 h, 8 h, and 24 h post-carrageenan injection. Baseline ankle caliper measurements were taken using one ankle with values rounded to one-thousandth of an inch. Measurements were confirmed as clinically normal by comparison with historical values for rats based on a range of body weights. Baseline measurements were then applied to both ankles, and these values remained with the animal so long as the ankle was clinically normal, with good definition in all ankle bones, and with no evidence of inflammation.

Necropsy and Hindpaw Weighing. At necropsy, approximately 24 h post-carrageenan injection, the animals were bled to exsanguination and euthanized by bilateral pneumothoracotomy. Hind paws were collected, weighed, and transected at the level of the medial and lateral malleolus.

Gait analysis scores in the vehicle groups had means of <1 on a scale of 0-6. Gait scores in treated rats did not differ significantly from vehicle controls, suggesting that gait is not the ideal pain measurement in the carrageenan model. Disease parameters in rats given oral or topical vehicles were generally similar with no statistically significant differences.

Figure 6A:
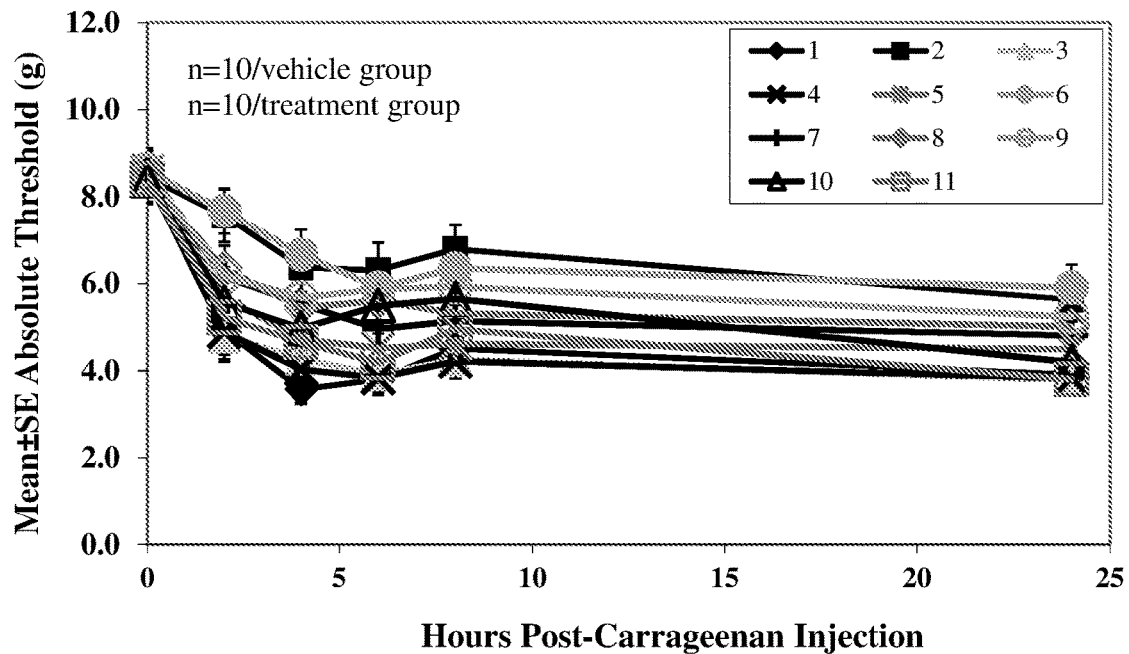
FIGS. 6A-6D depict the results of carrageenan-induced inflammation rat paw studies, comparing various topical naproxen formulations. Naprosyn®, Voltaren® (diclofenac) and Momendol (naproxen) topical gels and orally administered naproxen were also evaluated.
Figure 6B:
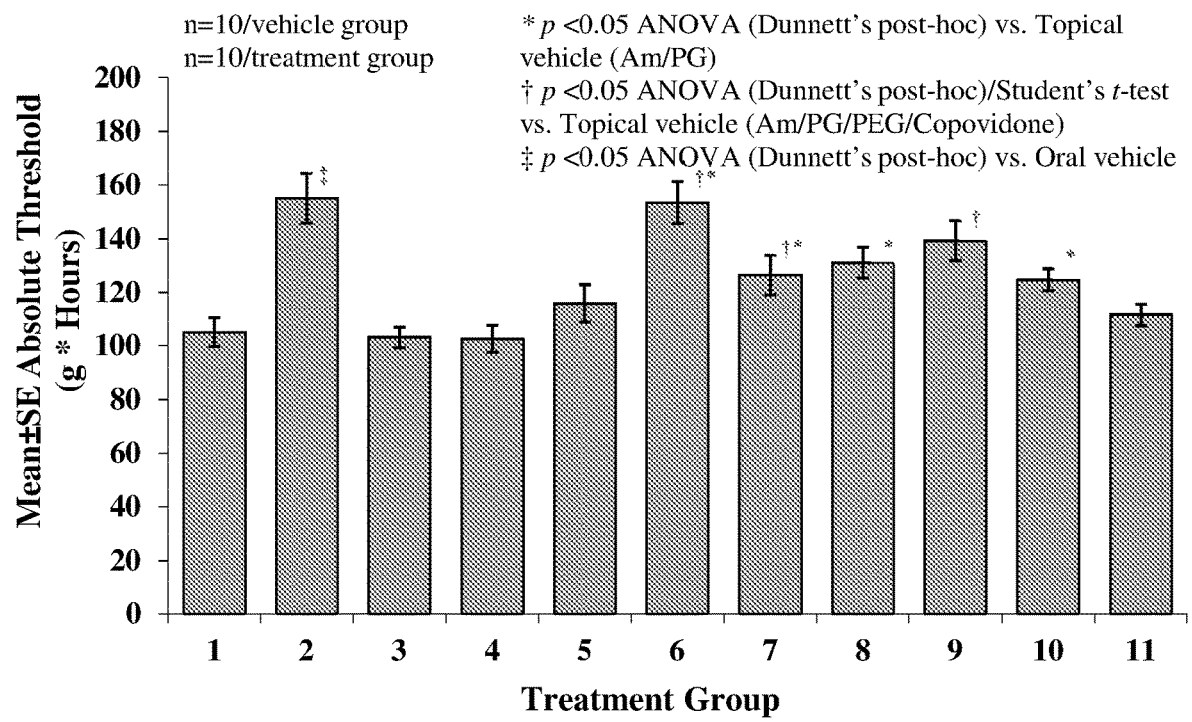
Figure 6C:
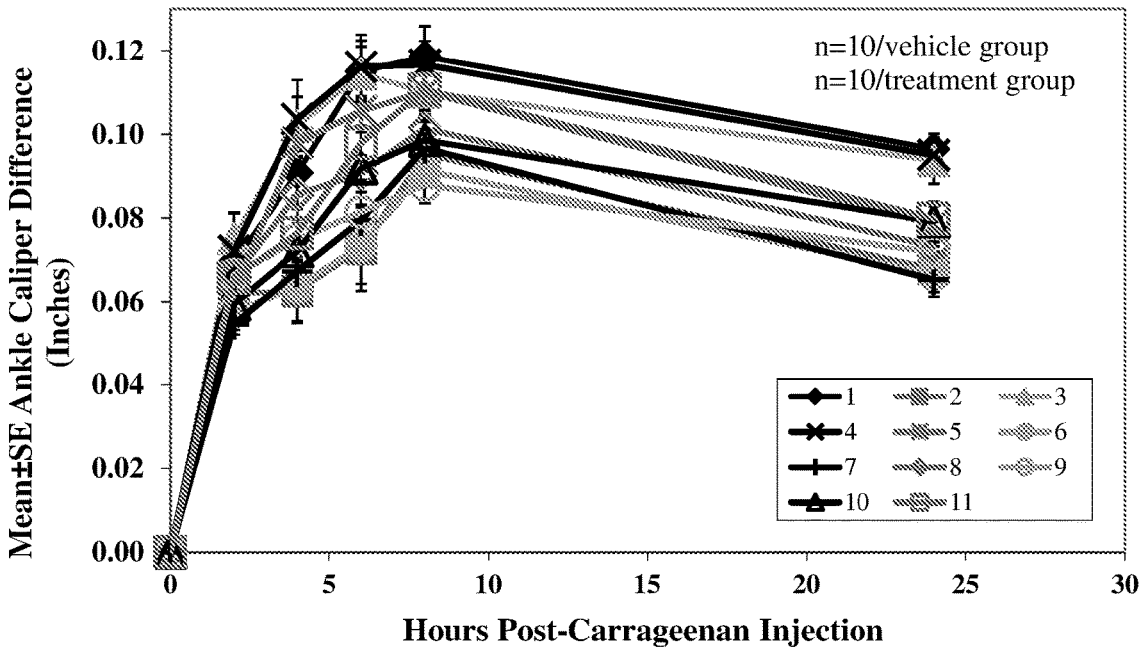
Figure 6D:
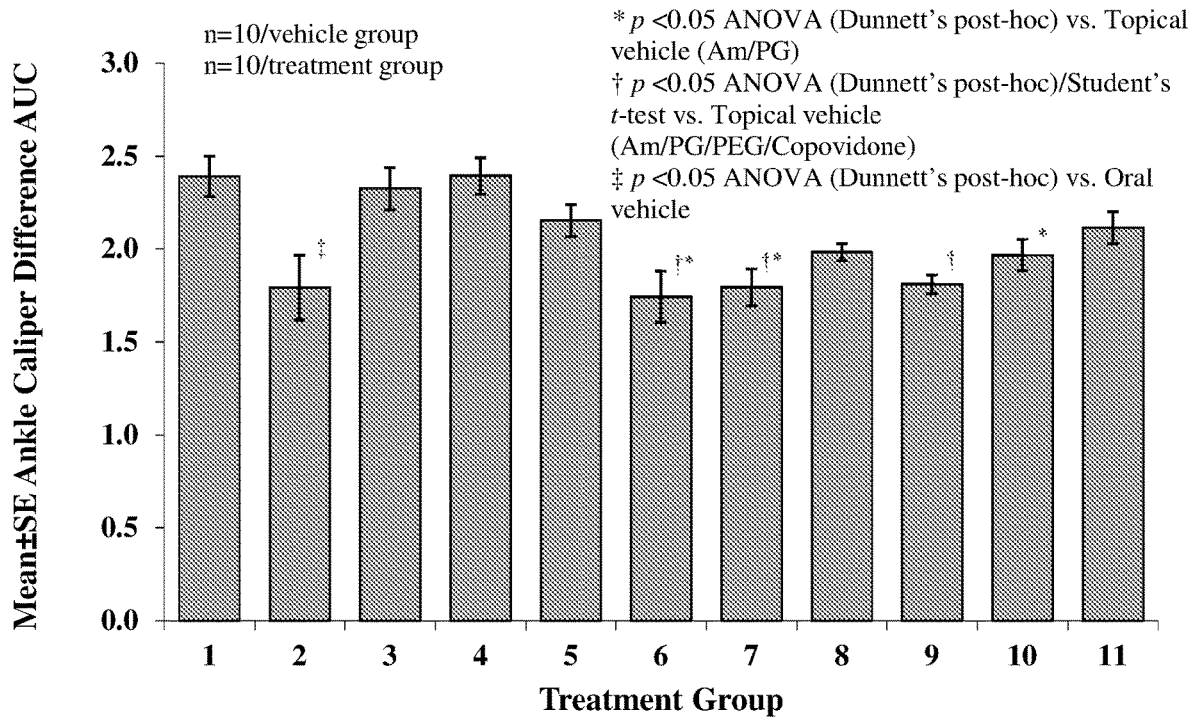

Table 12 shows the results of the von Frey analysis, ankle caliper measurements and post-mortem hindpaw weight differentials. The results of the von Frey analysis and ankle caliper measurements are also shown in FIGS. 6A-6D, over time (FIGS. 6A and 6C) and on average for the course of the study (FIGS. 6B and 6D).

TABLE 12

| Group | Treatment | Dose Conc (%) | Von Frey Absolute Threshold (g) AUC (Right Paw) | Ankle Diameter Difference (R − L) AUC | Paw Weight Difference (R − L) (g) |
|---|---|---|---|---|---|
| 1 | Oral vehicle (1% CMC/0.05% Tween ® 80) | 0 mg | 105.0 (5.4) | 2.39 (0.11) | 0.620 (0.025) |
| 2 | Naproxen (oral) | 12.5 mg | ‡155.1 (9.2) | ‡1.792 (0.174) | ‡0.410 (0.032) |
| 3 | Topical Vehicle (control) (Am/10%PG) | 0% | 103.1 (3.9) | 2.323 (0.115) | 0.627 (0.038) |
| 4 | Topical Vehicle (control) (Am/10%PG/ 10%PEG/ copovidone) | 0% | 102.5 (5.0) | 2.393 (0.099) | 0.656 (0.033) |
| 5 | Diclofenac Gel (Voltaren ®) | 2.32% | 115.8 (7.1) | 2.152 (0.86) | *†0.509 (0.038) |
| 6 | Naprosyn ® Gel | 10.0% | *†153.5 (7.8) | *†1.743 (0.137) | *†0.423 (0.031) |
| 7 | Momendol Gel | 10.0% | *†126.5 (7.4) | *†1.794 (0.098) | *†0.419 (0.016) |
| 8 | Naproxen Topical Gel, 10% w/w (Am/10%PG) | 10.0% | *131.1 (5.7) | 1.982 (0.045) | *0.470 (0.023) |
| 9 | Naproxen Topical Gel, 10% w/w (Am/10%PG/ 10%PEG/ copovidone) | 10.0% | †139.3 (7.4) | †1.810 (0.050) | *0.415 (0.024) |
| 10 | Naproxen Topical Gel, 10% w/w (Am/10%PG) | 5.0% | *124.8 (4.1) | *1.967 (0.085) | *0.492 (0.031) |
| 11 | Naproxen Topical Gel, 10% w/w (Am/10%PG) | 1.0% | 111.6 (4.1) | 2.114 (0.085) | 0.602 (0.033) |

(SE) = standard error in parentheses; AUC = area under the curve
Am = ammonia as neutralizing agent
*p < 0.05 ANOVA (Dunnett's post-hoc) vs. Topical vehicle (Am/PG)
†p < 0.05 ANOVA (Dunnett's post-hoc)/Student's t-test vs. Topical vehicle (Am/PG/PEG/Copovidone)
‡p < 0.05 ANOVA (Dunnett's post-hoc) vs. Oral vehicle Rats treated with oral Naproxen had both significantly increased von Frey absolute thresholds at all time points post-carrageenan injection (2-24 h) and a final weigh paw difference that was significantly reduced as compared to oral vehicle control rats. The von Frey absolute threshold expressed as area under the curve (AUC) was correspondingly increased significantly as compared to oral vehicle control. Rats treated orally with Naproxen had ankle caliper differences that were significantly reduced 4-6 h and 24 h post-carrageenan injection.

Among the topical controls, Naprosyn® showed the most prominent effect, showing statistically significant values across all three parameters. Momendol gel had von Frey absolute thresholds AUC that did not differ significantly from topical vehicle controls over time although the von Frey absolute threshold AUC was significantly increased by Momendol as compared to the topical controls. Rats treated topically with Momendol gel showed significantly reduced ankle caliper measurements over time and as AUC compared to the topical vehicles. Mean final paw weight differences were also significantly reduced with Momendol. Rats treated with Voltaren® had von Frey absolute thresholds and ankle caliper measurement difference AUC that did not differ significantly from the control vehicles. However, the mean final paw weight difference in rats treated with Voltaren® were significantly reduced as compared to the two topical vehicle formulations.

Topical treatment with 1%, 5%, or 10% naproxen gel in Am/PG vehicle or 10% in Am/PG/PEG/copovidone led to significant and dose responsive beneficial effects in the von Frey analysis and ankle caliper measurements. Treatment with 5% or 10% naproxen gel in the von Frey analysis, ankle caliper measurements and final hindpaw weight differentials. Naproxen gel administered at 10% in both formulations resulted in improvements that were statistically similar to the Naprosyn® gel treatment.

Example 4: In Vivo Evaluation: Rat Paw Test

The example below was conducted to evaluate the effect of various naproxen ammonium topical gel formulations (Table 13) on inflammation/edema induced by carrageenan-injection into the footpads of Sprague Dawley (SD) rats, as compared to the effects observed for commercially available (control) topical analgesic formulations including Naprosyn® Gel, Voltaren® Gel (diclofenac), and Lasonil® Gel (ibuprofen). The formulations shown in Table 13 below were applied to the respective animal subject three (3) hours prior to the carrageenan injection to induce swelling. Efficacy evaluation was based on von Frey absolute thresholds and ankle caliper differentials recorded over 24 h after initial carrageenan injection, and paw differential weights following euthanasia of the test subjects. Table 14 shows the compositions of the naproxen ammonium topical gel test formulations utilized for the treatment groups in Table 13.

TABLE 13

| Group | N | Treatment | Dose Level (mg/rat) | Dose Volume (μl/rat) | Dose Conc. (%) |
|---|---|---|---|---|---|
| 1 | 10 | Topical Vehicle (control) (Am/10%PG/10%PEG/copovidone) | 0 mg | 100 μL | 0% |
| 2 | 10 | Diclofenac Gel (Voltaren ®) | 2.32 mg | 100 μL | 2.32% |
| 3 | 10 | Naprosyn ® Gel | 10 mg | 100 μL | 10.0% |
| 4 | 10 | Naproxen Gel (Am/10%PG/10%PEG/copovidone) | 10 mg | 100 μL | 10.0% |
| 5 | 10 | Naproxen Gel (Am/2.5%PG/2.5% PEG) | 10 mg | 100 μL | 10.0% |
| 6 | 10 | Naproxen Gel (Am/2.5%PG/2.5% PEG) | 5 mg | 100 μL | 5.0% |
| 7 | 10 | Naproxen Gel (Am/2.5%PG/2.5% PEG) | 1 mg | 100 μL | 1.0% |
| 8 | 10 | Naproxen Gel (Am/2.5%PG/10% PEG) | 10 mg | 100 μL | 10.0% |
| 9 | 10 | Naproxen Gel (Am/2.5%PG/10% PEG) | 5 mg | 100 μL | 5.0% |
| 10 | 10 | Naproxen Gel (Am/2.5%PG/10% PEG) | 1 mg | 100 μL | 1.0% |
| 11 | 10 | Ibuprofen Gel (Lasonil ®) | 10 mg | 100 μL | 10.0% |

TABLE 14

| Functional Ingredient | Treatment Group # | | | | | | | |
|---|---|---|---|---|---|---|---|---|
| | #1 | #4 | #5 | #6 | #7 | #8 | #9 | #10 |
| Naproxen (% w/w) | 0% | 10.0% | 10.0% | 5.0% | 1.0% | 10.0% | 5.0% | 1.0% |
| Neutralizing Agent (% w/w) | 0.00% | 2.80% | 2.80% | Ammonia solution 1.40% | 0.30% | 2.80% | 1.40% | 0.30% |
| Gelling Agent | HEC H grade, 1.4% w/w | | | | | | | |
| Propylene Glycol (% w/w) | 10.0% | 10.0% | 2.5% | 2.5% | 2.5% | 2.5% | 2.5% | 2.5% |
| PEG 400 (% w/w) | 10.0% | 10.0% | 2.5% | 2.5% | 2.5% | 10.0% | 10.0% | 10.0% |
| Ethanol (% w/w) | 30.0% | 30.0% | 30.0% | 30.0% | 30.0% | 30.0% | 30.0% | 30.0% |
| Copovidone (% w/w) | 1.0% | 1.0% | 0% | 0% | 0% | 0% | 0% | 0% |
| Sodium metabisulfite | 0.10% | 0.10% | 0.10% | 0.10% | 0.10% | 0.10% | 0.10% | 0.10% |
| Glycerin | 0% | 0% | 0.50% | 0.50% | 0.50% | 0.50% | 0.50% | 0.50% |
| EDTA | 0% | 0% | 0% | 0% | 0% | 0% | 0% | 0% |
| Purified Water | Q.S. to 100% | | | | | | | |

Experimental Design. Male Sprague Dawley (Envigo RMS, Inc., Indianapolis) were weighed on Day 1 (mean 290 g) and randomized by body weight into 11 treatment groups. On Day 0-1, ten animals in each group were dosed with topical compounds on 2-minute intervals according to the dose schedules in Table 13. Three hours following treatment with the topical compounds, the animals were anesthetized and injected with carrageenan into the right hind paw. Von Frey analysis and ankle caliper measurements were conducted at time points of 2 h, 4 h, 6 h, 8 h, and 24 h post-carrageenan injection; caliper measurements were taken immediately following Von Frey analysis. Following conclusion of the live phase at 24-h post-carrageenan injection and completion of Von Frey analysis and ankle caliper measurements, the animals were immediately euthanized and hind paws were collected and weight.

Figure 7A:
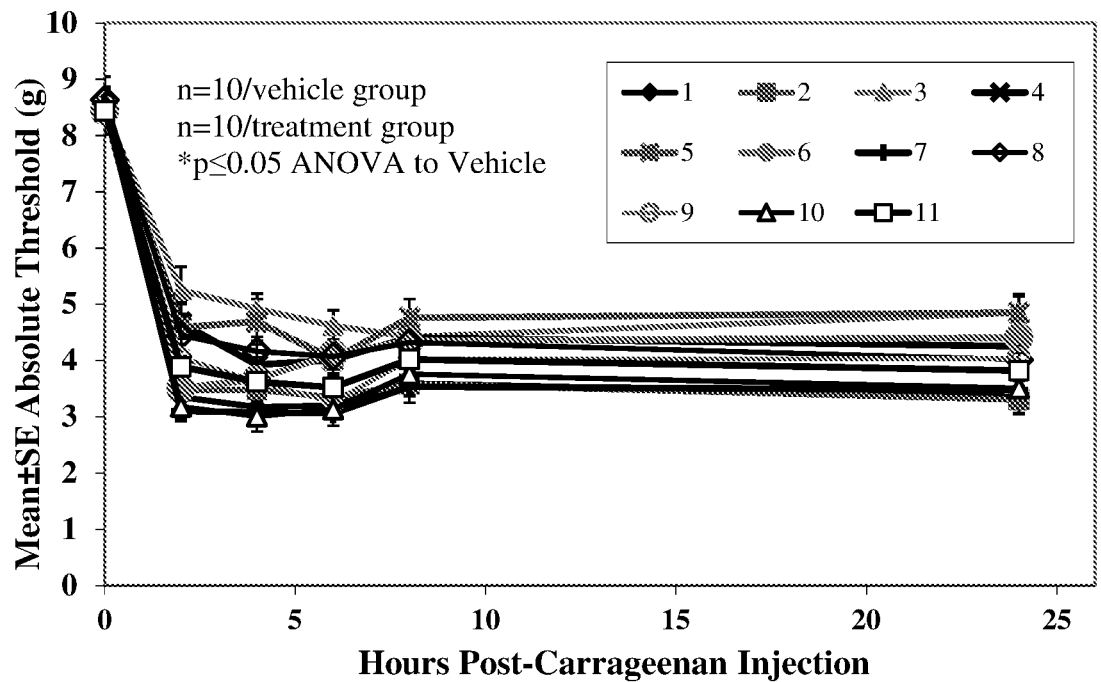
FIGS. 7A-7D depict the results of carrageenan-induced inflammation rat paw studies, comparing various topical naproxen formulations. Naprosyn®, Voltaren® (diclofenac) and Lasonil® (ibuprofen) topical gels were also evaluated.
Figure 7B:
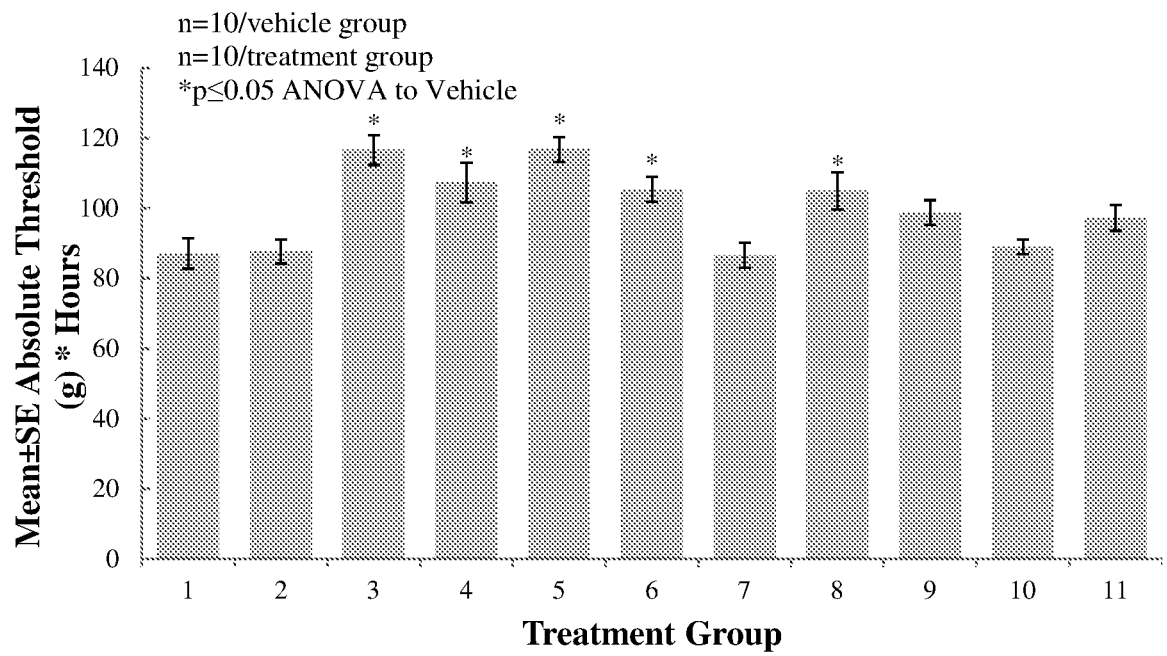
Figure 7C:
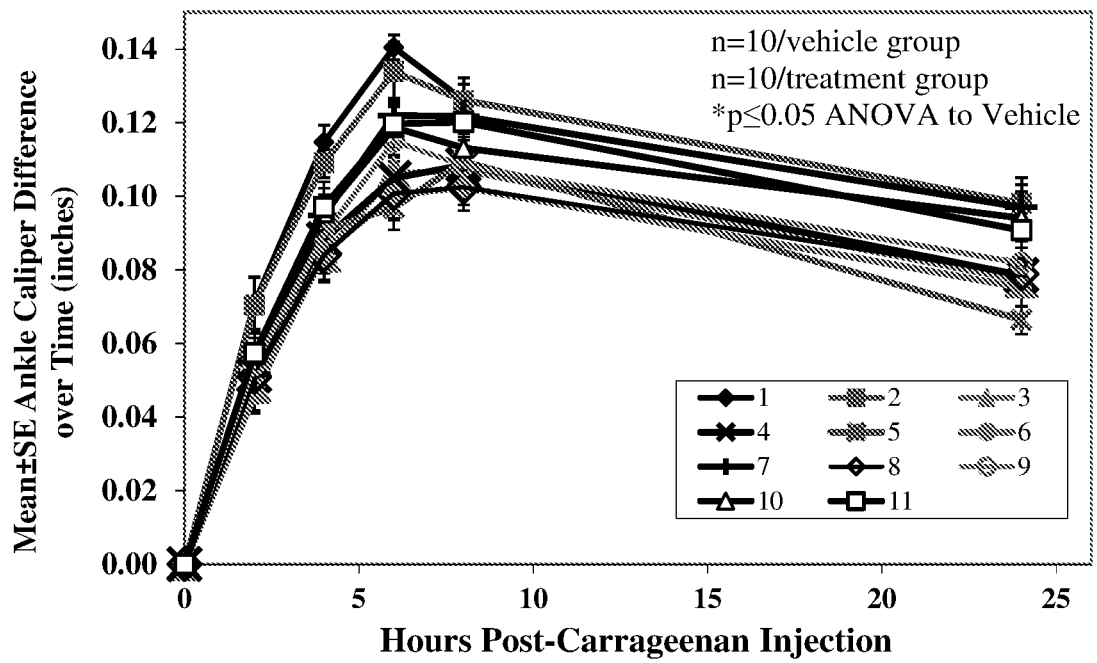
Figure 7D:
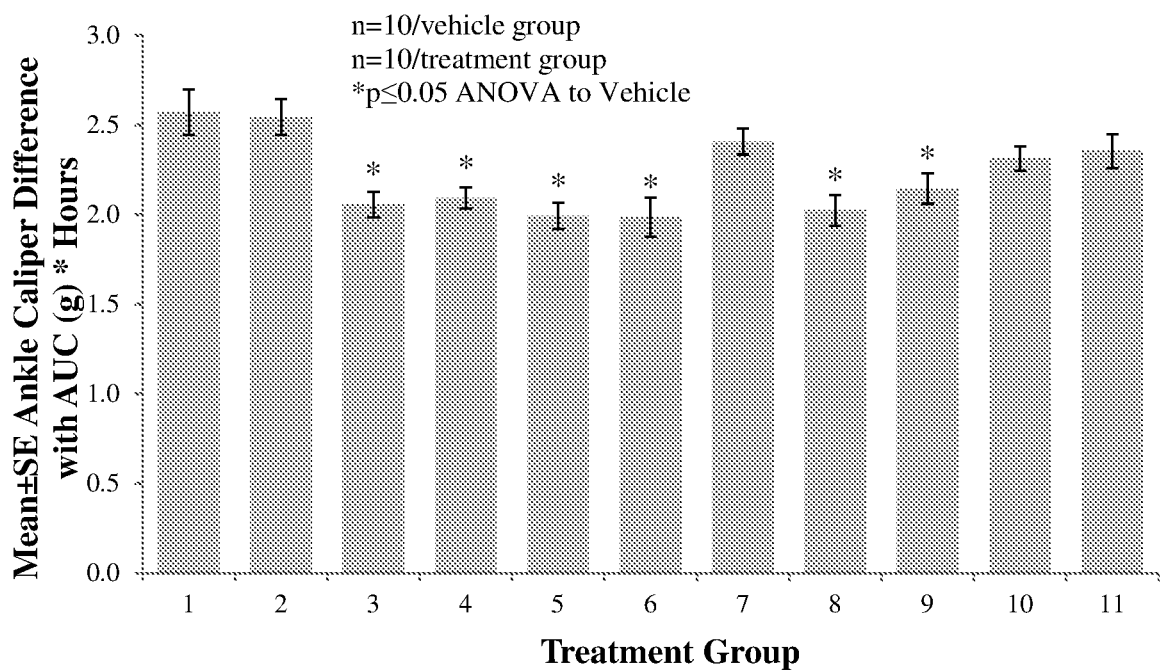

Von Frey analysis, ankle caliper measurements and post-mortem hindpaw weight differentials were recorded according to the protocols described in Example 3 above. Gait analysis was not conducted for these rat paw trials. Table 15 shows the results of the von Frey analysis, ankle caliper measurements and post-mortem hindpaw weight differentials. The results of the von Frey analysis and ankle caliper measurements are also shown in FIGS. 7A-7D, over time (FIGS. 7A and 7C) and on average for the course of the study (FIGS. 7B and 7D).

TABLE 15

| | Group Treatment | Dose Conc. (%) | Von Frey Absolute Threshold (g) AUC (Right Paw) | Ankle Diameter Difference (R − L) AUC | Paw Weight Difference (R − L) (g) |
|---|---|---|---|---|---|
| 1 | Topical Vehicle (control) (Am/10%PG/10%PEG/copovidone) | 0% | 87.1 (4.4) | 2.57 (0.13) | 0.9200 (0.0432) |
| 2 | Diclofenac Gel (Voltaren ®) | 2.32% | 87.6 (3.4) | 2.54 (0.10) | 0.9087 (0.0335) |
| 3 | Naprosyn ® Gel | 10.0% | *116.6 (4.3) | *2.06 (0.07) | *0.6839 (0.0386) |
| 4 | Naproxen Gel (Am/10%PG/10%PEG/copovidone) | 10.0% | *107.3 (5.6) | *2.09 (0.06) | 0.8075 (0.0284) |
| 5 | Naproxen Gel (Am/2.5%PG/2.5% PEG) | 10.0% | *116.8 (3.5) | *1.99 (0.07) | *0.7236 (0.0427) |
| 6 | Naproxen Gel (Am/2.5%PG/2.5% PEG) | 5.0% | *105.4 (3.5) | *1.99 (0.11) | *0.7229 (0.0262) |
| 7 | Naproxen Gel (Am/2.5%PG/2.5% PEG) | 1.0% | 86.6 (3.6) | 2.41 (0.07) | 0.8419 (0.0416) |
| 8 | Naproxen Gel (Am/2.5%PG/10% PEG) | 10.0% | *105.0 (5.3) | *2.02 (0.09) | *0.7349 (0.0363) |
| 9 | Naproxen Gel (Am/2.5%PG/10% PEG) | 5.0% | 98.7 (3.5) | *2.15 (0.09) | *0.7563 (0.0354) |

TABLE 15-continued

| Group | Treatment | Dose Conc. (%) | Von Frey Absolute Threshold (g) AUC (Right Paw) | Ankle Diameter Difference (R − L) AUC | Paw Weight Difference (R − L) (g) |
|---|---|---|---|---|---|
| 10 | Naproxen Gel (Am/2.5%PG/10% PEG) | 1.0% | 89.0 (2.0) | 2.31 (0.07) | 0.8284 (0.0533) |
| 11 | Ibuprofen Gel (Lasonil ®) | 10.0% | 97.2 (3.7) | 2.35 (0.09) | 0.8663 (0.0407) |

(SE) = standard error in parentheses; AUC = area under the curve
Am = ammonia as neutralizing agent
*p < 0.05 ANOVA (Dunnett's post-hoc) vs. Topical Vehicle Naprosyn® showed the most prominent effect among all topical control gels, across all three parameters. Voltaren® and Lasonil® gel results were not significant. Topical treatment with 10% naproxen gel in PG/PEG/copovidone (Treatment group #4) led to significant beneficial effect in the von Frey analysis and ankle caliper measurements. Treatment with 5% or 10% naproxen gel in 2.5% PG and 2.5% PEG (treatment groups #8 and 9) resulted in significant and dose responsive beneficial effects in the von Frey analysis, ankle caliper measurements and final hindpaw weight differentials. Topical treatment with naproxen gel at 1%, 5%, and 10% in 2.5% PG and 10% PEG provided significant and dose responsive effects in ankle caliper measurements, with the mid to high dose showing significant effect on the final hindpaw weight differentials, and the high dose providing significant effect in observed von Frey threshold. Naproxen gel administered at 10% w/w in all three formulations demonstrated statistically similar improvements as with Naprosyn®.

Example 5: In Vivo Evaluation: Minipig Dermal Penetration Assay

A minipig dermal penetration study was conducted in order to evaluate and confirm the bioavailability of naproxen in target tissue areas (muscle) following dermal application of various naproxen ammonium topical gel compositions as compared to Naprosyn®. Eight different naproxen formulations, including Naprosyn® as control, were evaluated. Six of the test naproxen formulations were selected for the minipig dermal penetration assay based on observed efficacy in the rat paw studies in Example 4 (2 formulations—2.5% PG and 2.5% PEG, or 2.5% PG and 10% PEG—at 3 different naproxen concentrations—1% w/w, 5% w/w and 10% w/w) and the seventh naproxen formulation was selected from Example 3 (10% naproxen, Am/10% PG only) based on its high in vitro flux observed in Franz cell diffusion tests. The eight different naproxen formulations are listed below in Table 16.

TABLE 16

| Group | Formulation | | Naproxen (% w/w) in Formulation | Number of Female Animals in Study |
|---|---|---|---|---|
| 1 | Naprosyn ® 10% Gel | n/a | 10.0% | 8 |
| | Naproxen Topical Gel, 1% w/w (Rat paw, Ex. 4, Group #7) | Ammonia 2.5% PG | 1.0% | |
| | Naproxen Topical Gel, 5% w/w (Rat paw, Ex. 4, Group #6) | 2.5% PEG | 5.0% | |

TABLE 16-continued

| Group | Formulation | | Naproxen (% w/w) in Formulation | Number of Female Animals in Study |
|---|---|---|---|---|
| | Naproxen Topical Gel, 10% w/w (Rat paw, Ex. 4, Group #5) | | 10.0% | |
| | Naproxen Topical Gel, 1% w/w (Rat paw, Ex. 4, Group #10) | Ammonia 2.5% PG | 1.0% | |
| | Naproxen Topical Gel, 5% w/w (Rat paw, Ex. 4, Group #9) | 10% PEG | 5.0% | |
| | Naproxen Topical Gel, 10% w/w (Rat paw, Ex. 4, Group #8) | | 10.0% | |
| | Naproxen Topical Gel, 10% w/w (Rat Paw, Ex. 3, Group #8) | Ammonia 10% PG | 10.0% | |

Each formulation was applied to eight female minipig test subjects for evaluation of dermal penetration. The same eight minipig test subjects were used for evaluation all eight formulations to allow for intra-individual comparison. The formulations were applied to the minipig subjects twice daily, with a 10 mg/cm$^2$ area dose (60 mg formulation to a 2 cm×3 cm, 6 cm$^2$, dermal dose site) with each application to approximate clinical use conditions. After 5 doses, the tissue levels of naproxen in skin and muscle compartments were determined by LC-MS analysis.

Figure 8A:
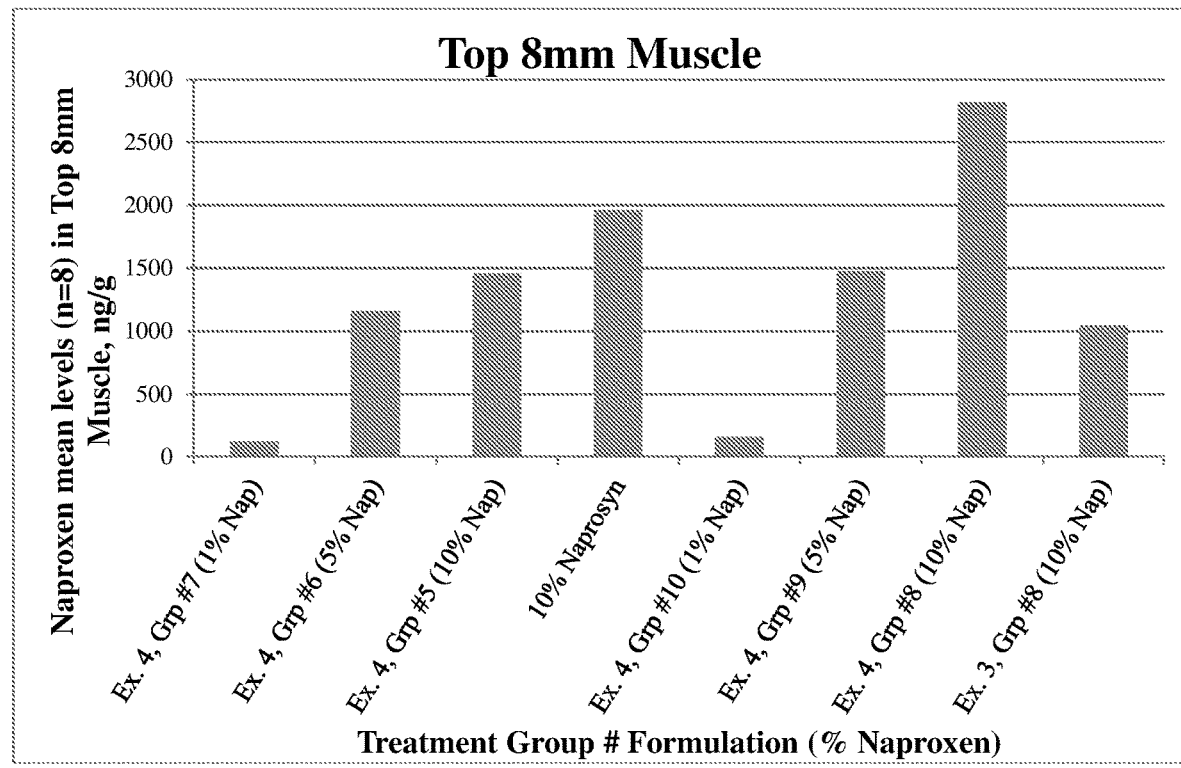
FIGS. 8A-8D depict tissue levels of naproxen measured in muscle and skin tissue in Minipig Dermal Penetration studies for various topical formulations of naproxen using ammonia solution as a neutralizing agent.
Figure 8B:
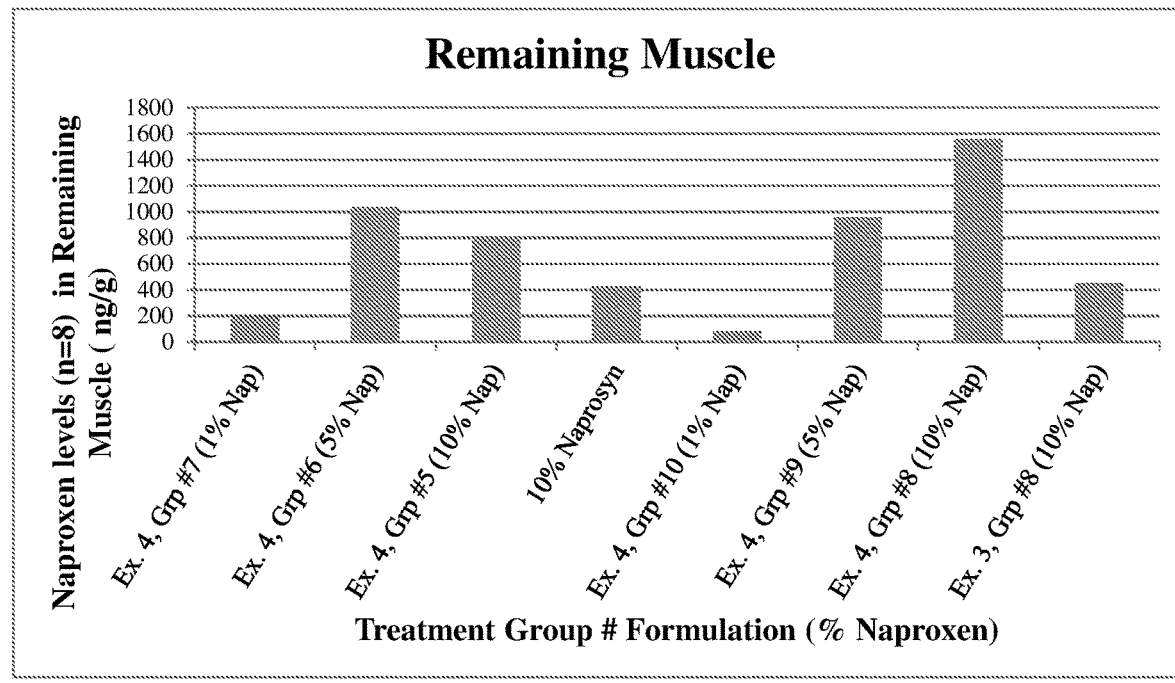
Figure 8C:
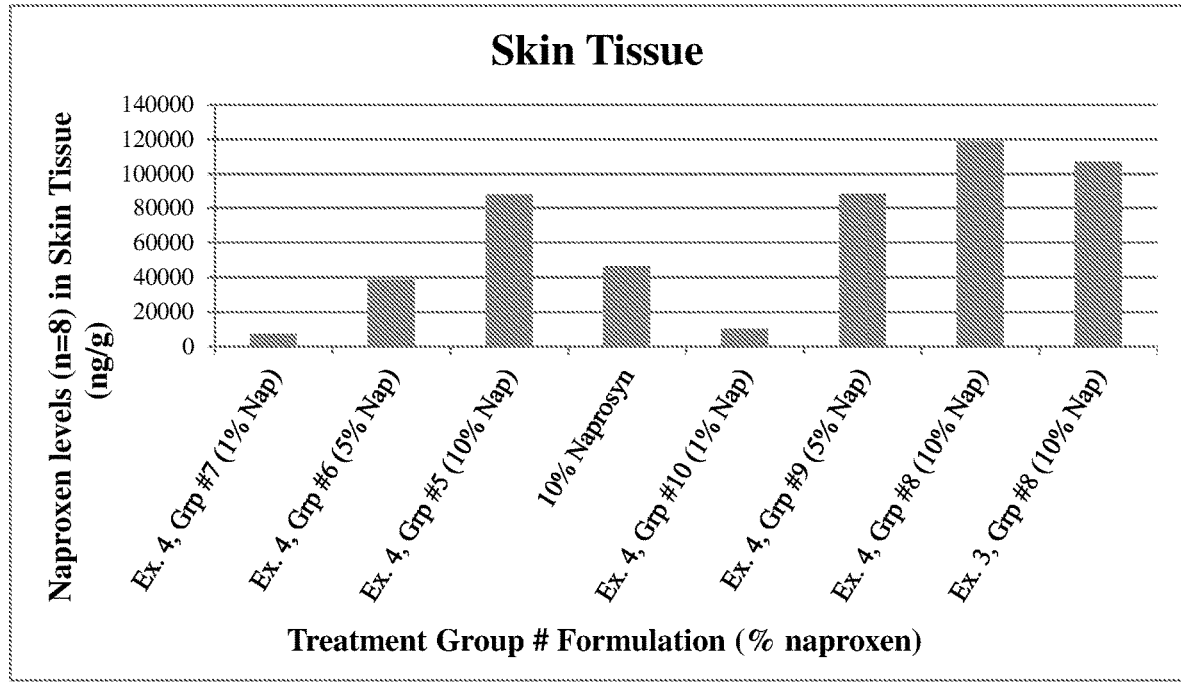
Figure 8D:
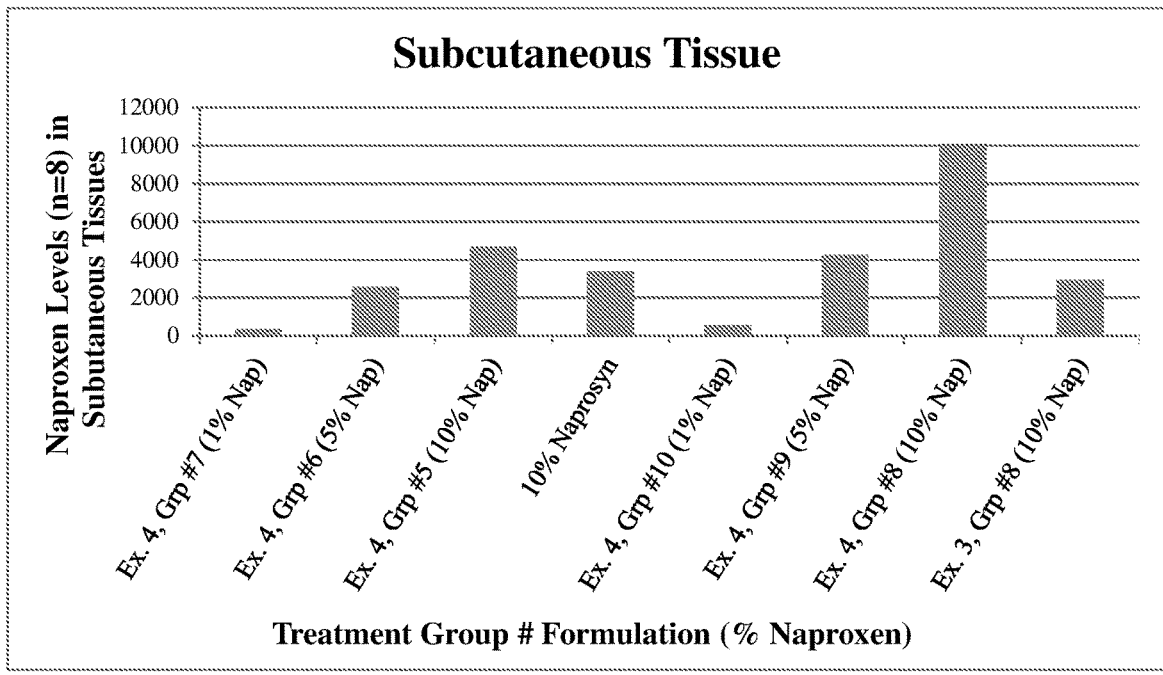

FIGS. 8A-8D show the observed mean levels of naproxen in muscle tissue (FIGS. 8A and 8B) and in skin tissue (FIGS. 8C and 8D). The levels of naproxen in muscle and skin tissues observed with application of 1% w/w naproxen topical gel formulations was less than those achieved with Naprosyn® gel, 10% w/w. For the 5% w/w and 10% w/w naproxen gel compositions, excepting the formulation containing propylene glycol only, showed comparable or improved penetration into muscle and skin tissues. In particular, the topical gel formulation containing 10% w/w naproxen in 2.5% PG and 10% PEG demonstrated superior tissue penetration.

Example 6: Exemplary Topical Gel Composition Preparation

An exemplary formulation for a clear, aqueous topical gel composition was prepared according to ingredient list shown in Table 17 below. The excipient concentrations were selected based upon the results observed in vitro permeation tests, rat paw studies, and minipig dermal absorption trials in Examples 1-5 above. EDTA was added to the composition as a co-antioxidant to sodium metabisulfite.

TABLE 17

| Functional Ingredient | Concentration (% w/w) |
| --- | --- |
| Naproxen | 10.0% |
| Ammonia solution | 2.80% |
| Gelling Agent, HEC H grade | 1.40% |
| Propylene Glycol | 2.50% |
| PEG 400 | 10.0% |
| Ethanol | 30.0% |
| Sodium metabisulfite | 0.25% |
| Glycerin | 0.50% |
| EDTA | 0.17% |
| Purified Water | Q.S. 100% |

What is claimed is:

1. A topical gel composition, comprising:
the ammonium salt of naproxen;
one or more gelling agents; and
water,
wherein the one or more gelling agents comprise hydroxyethylcellulose,
wherein the topical gel composition comprises propylene glycol and polyethylene glycol, and
wherein the topical gel composition has a total concentration of naproxen of at least 1% w/w.

2. The topical gel composition of claim 1, wherein the topical gel composition has a total concentration of naproxen between 1% w/w and 20% w/w.

3. The topical gel composition of claim 1, wherein the topical gel composition comprises at least about 25% w/w water.

4. The topical gel composition of claim 1, wherein the topical gel composition comprises at least 1.0% w/w one or more gelling agents.

5. The topical gel composition of claim 1, wherein the topical gel composition comprises ethanol.

6. The topical gel composition of claim 5, wherein the topical gel comprises at least 30% w/w ethanol.

7. The topical gel composition of claim 1, wherein the topical gel composition comprises between 1% w/w and 10% w/w propylene glycol.

8. The topical gel composition of claim 1, wherein the topical gel composition comprises between 2.5% w/w and 20% w/w polyethylene glycol.

9. The topical gel composition of claim 1, wherein the topical gel composition comprises between 5% w/w and 20% w/w of a combination of propylene glycol and polyethylene glycol.

10. The topical gel composition of claim 1, wherein the topical gel composition further comprises one or more pharmaceutically acceptable excipients selected from the group consisting of one or more antioxidants, one or more preservatives, one or more sensates, and fragrance.

11. The topical gel composition of claim 1, wherein the topical gel composition further comprises between 0.1% w/w and 0.25% w/w sodium metabisulfite.

12. The topical gel composition of claim 1, wherein the topical gel composition further comprises between 0.1% w/w and 0.20% w/w EDTA.

13. The topical gel composition of claim 1, wherein the topical gel composition further comprises between 0.1% w/w and 1.0% w/w glycerin.

14. The topical gel composition of claim 1, wherein the topical gel composition comprises one or more film-forming agents.

15. The topical gel composition of claim 1, wherein the topical gel composition comprises copovidone.

16. The topical gel composition of claim 1, wherein the topical gel composition has a pH of between pH 7 and pH 9.

17. The topical gel composition of claim 1, wherein the topical gel composition has a viscosity of between 7,000 cP and 11,000 cP.

18. The topical gel composition of claim 1, wherein the topical gel composition is a clear gel.

19. The topical gel composition of claim 1, wherein the topical gel composition has a dermal absorption of naproxen into the epidermis and dermis of at least 5 μg/cm$^2$ as determined by an in vitro permeation test.

20. The topical gel composition of claim 1, wherein the topical gel composition has a flux of at least 0.20 μg/cm$^2$/h as determined by an in vitro permeation test.

21. The topical gel composition of claim 20, wherein the topical gel composition has a flux of between 0.20 μg/cm$^2$/h and 2.00 μg/cm$^2$/h as determined by an in vitro permeation test.

22. The topical gel composition of claim 1, wherein the topical gel composition has a skin permeation/accumulation ratio of between 1:3 and 1:1.

23. A method of treating muscle pain or joint pain in a patient in need thereof, comprising applying a topical gel composition according to claim 1, to the patient's skin at the site of pain.

24. The method of claim 23, wherein the muscle pain or joint pain is associated with arthritis, sprains, strains, bruises, or backache.

25. The method of claim 23, wherein the topical gel composition remains transparent on the patient's skin for at least 1 hour after application.

26. The method of claim 23, wherein the topical gel composition remains transparent on the patient's skin at least four hours after application.

27. A method of preparing a topical gel composition of claim 1, comprising:
combining a gelling agent and water to provide a gel mixture;
adding an ammonia solution to the gel mixture;
combining naproxen free acid, and one or more alcohol solvents to provide an alcohol mixture; and
combining the alcohol mixture with the gel mixture to provide the topical gel composition,
wherein the alcohol solvents comprise propylene glycol and polyethylene glycol.

28. The method of claim 27, wherein the quantity of the ammonia solution is greater than or equal to one molar equivalent of the quantity the naproxen free acid.

29. The method of claim 27, wherein the one or more alcohol solvents comprises ethanol.

* * * * *

UNITED STATES PATENT AND TRADEMARK OFFICE
CERTIFICATE OF CORRECTION

PATENT NO. : 12,274,683 B2
APPLICATION NO. : 17/425746
DATED : April 15, 2025
INVENTOR(S) : Olufoyekemi Badejo It is certified that error appears in the above-identified patent and that said Letters Patent is hereby corrected as shown below:

In the Specification

In Column 2, Line 66, delete "the under" and insert -- under the --, therefor.

In Column 3, Line 14, delete "the under" and insert -- under the --, therefor.

In Column 5, Line 13, delete "such" and insert -- such as --, therefor.

In Column 5, Line 14, delete "found" and insert -- found to --, therefor.

In Column 8, Line 41, delete "carrageenates," and insert -- carrageenans, --, therefor.

In Column 8, Line 44, delete "w/w" and insert -- w/w of --, therefor.

In Column 8, Line 46, delete "w/w" and insert -- w/w of --, therefor.

In Column 9, Line 16, delete "w/w" and insert -- w/w of --, therefor.

In Column 10, Line 66, delete "combination" and insert -- combination of --, therefor.

In Column 15, Line 50, delete "product" and insert -- produce --, therefor.

In Column 17, Line 51, delete "w/w" and insert -- w/w of --, therefor.

In Column 20, Line 41, delete "C892)" and insert -- C892 --, therefor.

In Column 20, Line 59, delete "where" and insert -- were --, therefor.

In Column 22, Line 32, delete "where" and insert -- were --, therefor.

Signed and Sealed this
Twelfth Day of August, 2025

Coke Morgan Stewart
*Acting Director of the United States Patent and Trademark Office*

CERTIFICATE OF CORRECTION (continued)
U.S. Pat. No. 12,274,683 B2

In Column 24, Line 32, delete "where" and insert -- were --, therefor.

In Column 28, Line 10, delete "testing" and insert -- testing. --, therefor.

In Column 29, Line 43, delete "weigh" and insert -- weight --, therefor.

In Column 34, Line 35, delete "evaluation" and insert -- evaluation of --, therefor.

In the Claims

In Column 35, Line 33, in Claim 4, delete "w/w" and insert -- w/w of --, thereof.

In Column 36, Line 56, in Claim 28, delete "quantity" and insert -- quantity of --, thereof.